(12) United States Patent
Podoleanu

(10) Patent No.: US 8,472,027 B2
(45) Date of Patent: Jun. 25, 2013

(54) SPECTRAL INTERFEROMETRY METHOD AND APPARATUS

(75) Inventor: Adrian Podoleanu, Canterbury (GB)

(73) Assignee: University of Kent, Canterbury, Kent (GB)

( * ) Notice: Subject to any disclaimer, the term of this patent is extended or adjusted under 35 U.S.C. 154(b) by 0 days.

(21) Appl. No.: 13/178,695

(22) Filed: Jul. 8, 2011

(65) Prior Publication Data

US 2012/0062898 A1    Mar. 15, 2012

Related U.S. Application Data

(63) Continuation of application No. 10/576,069, filed as application No. PCT/GB2004/004351 on Oct. 14, 2004, now Pat. No. 7,995,207.

(30) Foreign Application Priority Data

Oct. 14, 2003 (GB) .................................. 0324062.9

(51) Int. Cl.
G01B 9/02 (2006.01)

(52) U.S. Cl.
USPC ........................................................ 356/451

(58) Field of Classification Search
USPC ............. 356/451, 479, 497, 520, 521
See application file for complete search history.

(56) References Cited

U.S. PATENT DOCUMENTS

| 4,932,782 | A | 6/1990 | Graindorge et al. |
| 5,317,389 | A | 5/1994 | Hochberg et al. |
| 5,565,986 | A | 10/1996 | Knuttel |
| 5,642,194 | A | 6/1997 | Erskine |

(Continued)

FOREIGN PATENT DOCUMENTS

| JP | 2001-229106 | 8/2001 |
| JP | 2001-272332 | 10/2001 |
| JP | 2005-242792 | 9/2005 |

OTHER PUBLICATIONS

A. L. King and R. Davis in "The Curious Bands of Talbot", American Journal of Physics, vol. 39, (1971), pp. 1195-1198.

(Continued)

Primary Examiner — Tarifur Chowdhury
Assistant Examiner — Jonathon Cook
(74) Attorney, Agent, or Firm — Nixon Peabody LLP; Jeffrey L. Costellia

(57) ABSTRACT

A spectral interferometry apparatus and method is provided to supply unambiguous profiles (A-scans free of mirror terms) of the reflectivity versus optical path difference and make difference between the positive and negative optical path difference or provide output in a selected interval of optical path differences. The apparatus comprises object optics that transfer a beam from an optical source to a target object (55) to produce an object beam and reference optics that produce a reference beam. Displacing means (57) are provided to produce a gap (g) between the object beam (41') and the reference beam (42'). Optical spectrum dispersing means (7) such as a grating or a prism receive the two relatively displaced beams, and disperse their spectral content onto a reading element such as a CCD. The combination of the displacing means and the optical spectrum dispersing means creates an intrinsic optical delay between the wavetrains of the object beam and the reference beam which can be used with the optical path difference in the interferometer to generate a channelled spectrum for the optical path difference in the interferometer on the reading element.

12 Claims, 12 Drawing Sheets

U.S. PATENT DOCUMENTS

| | | | |
|---|---|---|---|
| 6,072,765 | A | 6/2000 | Rolland et al. |
| 6,396,587 | B1 | 5/2002 | Knupfer et al. |
| 7,167,249 | B1 | 1/2007 | Otten, III |
| 7,355,716 | B2 | 4/2008 | de Boer et al. |
| 2005/0018201 | A1* | 1/2005 | de Boer et al. ............... 356/479 |

OTHER PUBLICATIONS

M. Parker Givens, "Talbol's bands", American Journal of Physics, 61, (7), (1993), pp. 601-605.

R. Leitgeb, M. Wojtkowski, A. Kowalczyk, C. K. Hizenberger, M. Sticker, and A. F. Fercher, "Spectral Measurement of Absorption by Spectroscopic Frequency-domain Optical Coherence Tomography", Optics Letters, vol. 25, 11/Jun. 1, 2011, pp. 820-822.

A. Gh. Podoleanu, S. Taplin, D. J. Webb and D. A. Jackson, "Channeled Spectrum Display using a CCD Array for Student Laboratory Demonstrations", European J. Phys., 15, (1994), pp. 266-271.

S. R. Taplin, A. Gh. Podoleanu, D. J. Webb and D. A. Jackson, "White-light Displacement Sensor Incorporation Signal Analysis of Channeled Spectra", ISPIE vol. 2292 Fiber Optic and Laser Sensors XII (1994), pp. 94-100.

G. Hausler and M. W. Lindner, "Coherence Radar and Spectral Radar—New Tools for Dermatological Diagnosis", J. Biomed Optics, Jan. 1998 D, vol. 3, No. 1, pp. 21-31.

M. Wojtkowski, A. Kowalczyk, P. Targowski, 1. Gorczynsk, "Fourier-domain Optical Coherecr Tomography: Next Step in Optical Imaging", Optica Applicata, vol. XXXII, No. 4, (2002), pp. 569-580.

A. Gh. Podoleanu, S. Taplin, D. J. Webb and D.A. Jackson, "Theoretical Study of Talbot-like Bands Observed Using a Laser Diode Below Threshold", Published in J. Pure and Applied Optics, vol. 7, (1998), pp. 517-536.

A. Gh. Podoleanu, S. Taplin, D. J. Webb, D.A. Jackson, Talbot-like Bands for Laser Diode Below Threshold, J. Pure and Applied Optics, vol. 6, Issuer 3, (1997), pp. 413-424.

Preliminary Notice of Reasons for Rejection, Japanese Patent Application No. 2006-534818.

* cited by examiner

SPECTRAL INTERFEROMETRY METHOD AND APPARATUS

BACKGROUND OF THE INVENTION

1. Field of the Invention

The present invention relates to a spectral interferometry apparatus and method, which can be used to supply unambiguous profiles of the reflectivity versus optical path difference and recognise positive from negative values of optical path difference.

2. Description of the Related Art

There is a growing interest in the application of low coherence interferometry in the general field of sensing. Low coherence interferometry methods provide absolute distance measurements and are well suited for imaging rough reflecting surfaces or producing slices in the volume of diffusive and scattering media. There are different methods which obtain depth resolved information using low-coherence optical sources, and one such method uses dispersion of the spectrum. The periodicity of the channelled spectrum is proportional to the optical path difference (OPD) in an interferometer, as described as long ago as 1837, as the so called "curious bands of Talbot". Recent presentations of such an old phenomenon are reported by A. L. King and R. Davis in "The Curious Bands of Talbot" published in the American Journal of Physics, vol. 39, (1971), p. 1195-1198 and by M. Parker Givens, "Talbot's bands", American Journal of Physics, 61, (7), (1993), p. 601-605.

Channelled spectrum methods have been used in the sensing and fiber optic sensing field. Recent implementations have used photodetector or CCD arrays to display the channelled spectrum, as disclosed in "Channeled Spectrum Display using a CCD Array for Student Laboratory Demonstrations", published by A. Gh. Podoleanu, S. Taplin, D. J. Webb and D. A. Jackson in the European J. Phys., 15, (1994), p. 266-271.

Channelled spectrum has also been employed in a method called "spectral optical coherence tomography" (SOCT), as disclosed in "Coherence Radar and Spectral Radar—New Tools for Dermatological Diagnosis", published by G. Hausler and M. W. Lindner, in J. Biomed Optics, January 1998 D, Vol. 3 No. 1, pp. 21-31 and disclosed in the following patents: U.S. Pat. No. 4,932,782, Channelled light spectrum measurement method and device, P. Graindorge; U.S. Pat. No. 5,317,389; Method and apparatus for white-light dispersed-fringe interferometric measurement of corneal topography, Hochberg et al. Further such methods have been disclosed in U.S. Pat. No. 6,072,765, Optical Disk Readout Method using Optical Coherence tomography and Spectral Interferometry, by J. P. Rolland and P. J. Delfyett. The advantage of the spectral methods is that the OPD information is translated into the periodicity of peaks and troughs in the channelled spectrum and no mechanical means are needed to scan the object in depth, in for example, optical coherence tomography (OCT) of tissue. Furthermore, no mechanical means are needed to explore the OPD in multiplexed sensor arrays in such methods. If multi-layered objects are imaged, such as tissue, each layer will imprint its own channelled spectrum periodicity, depending on its depth, with the amplitude of the spectrum modulation proportional to the square root of the reflectivity of that layer. A fast Fourier transform (FFT) of the spectrum of a charge coupled device (CCD) signal translates the periodicity of the channelled spectrum into peaks of different frequency, with the frequency directly related to the path imbalance. Such a profile is termed as an A-scan in OCT, i.e. a profile of reflectivity in depth.

A possible bulk implementation of a prior art SOCT apparatus is shown in FIG. 1. In this arrangement, an optical beam from a source 1 is collimated by a collimating element 2, which could be a simple lens or achromat, or a mirror or combination of lenses or mirrors, to form the beam 3. The beam 3 is then directed towards a beam-splitter 4. The source 1 is broadband and may be for example one or more light emitting diodes, superluminiscent diodes, bulb lamps or short-pulse lasers combined to produce the largest possible bandwidth and minimum spectrum ripple by techniques known in the art. The source 1 has a central wavelength suitable for the particular object to be investigated. For the investigation of a patient's eye using OCT, a wavelength in the near infrared, such as 800 to 900 nm is used. For examining skin, a wavelength of 1300 nm may be used. For sensing applications, wavelengths in the telecommunication band of 1500 nm are preferably used.

The light received by the beam-splitter 4 is split into a first optical path 41 leading to a mirror object 5, and into a second optical path 42 leading to a reference mirror 6. After reflection on the two mirrors 5 and 6 and after crossing the beam-splitter 4, the resulting two beams are superposed on an optical spectrum dispersing means, 7, for spectral analysis. The optical spectrum dispersing means 7 could be one or more diffraction gratings, one or more prisms, or combination of prisms or gratings. In the optical spectrum dispersing means 7 the spectrum is dispersed (when using a prism or prisms) or diffracted (when using a diffraction grating or gratings), and a fan of rays with different wavelengths is output. This is subsequently focused by a focusing element 8 onto a reading element, a linear photodetector array or a CCD linear array 9. An electrical spectrum analyser 91 provides the FFT of the signal delivered by the reading element 9.

The distance from the beam splitter 4 to the mirror 5 is denoted by Z. However, in other prior art arrangements, in which the mirror is replaced by a thick scattering, multi-layer object, Z is the distance from the beam splitter 4 to a scattering point or layer within the object. This means that the object path is 2Z. The distance between the beam splitter 4 and the mirror 6 is X, which means that the length of the reference path is 2x.

The channelled spectrum periodicity depends on the OPD, defined as:

$$OPD = 2(Z-X)$$

Consider the arrangement in which the mirror 5 is replaced by a thick scattering multi-layer object. In this case, as the periodicity depends on the modulus of the OPD, scatterers or layers symmetrically placed around the position at which the OPD is zero give the same periodicity in the channelled spectrum. If Fourier transformed, besides the terms corresponding to the useful range of OPDs, symmetrically placed terms are obtained, often referred as mirror terms and a problem associated with Fourier domain OCT can be termed as the problem of mirror terms. This introduces errors in the depth profile of the OCT system used for imaging. Equivalently when channelled spectrum is used for sensing, there is a cross-talk of signals from sensors placed at the same value of OPD either side of the zero point. Therefore, all the prior art spectral (Fourier domain) OCT methods discussed above rely on an adjustment of the object position in such a way that the scatterers in the depth of the object are confined within a single sign range of OPDs, i.e. either positive or negative. Such an adjustment complicates the measurement procedure, and may not be applicable in all situations.

For the purposes of this description, the OPD in the interferometer will be defined as the Object Path Length minus the Reference Path Length. For example, if the object to be examined is the retina, then the origin of OPD could be set somewhere in the vitreous, in front of the retinal nerve fiber layer. This will mean that the retina scatterers are all at positions such that the OPD is greater than zero. However, if the vitreous has defects within the same path range, then these defects will appear in the final depth profile of the retina. Thus, a need exists for procedures to eliminate the peaks outside the interesting range, or to make the system sensitive to the sign of the OPD.

A method called "phase shifting spectral interferometry" has recently been introduced to eliminate the terms for one sign of the OPD range, in order to address the problem of mirror terms. By introducing exact phase shifts between the two optical interferometer paths of successive CCD frames, and combining the spectra collected, it is possible to reduce the noise as well as eliminate one of the autocorrelation terms in the electrical Fourier transform spectrum of the CCD signal (for positive or negative OPD). The method allows correct reconstruction of layers in depth. However, phase shifting spectral interferometry has the following disadvantages. The phase shifts have to be accurate to within a few degrees, which requires precise control of the movement of the reference mirror. Also, because the final spectrum is delivered only after at least a number M of spectra are collected, the process is M times slower than conventional methods. A method of phase shifting spectral interferometry using five steps was disclosed in: "Fourier-domain optical coherence tomography: next step in optical imaging", by M. Wojtkowski, A. Kowalczyk, P. Targowski, I. Gorczynska, published in Optica Applicata, Vol. XXXII, No. 4, (2002), p. 569-580. When using this method, five frames are required before providing an OCT image. However, the most important disadvantage associated with phase shifting spectral interferometry is movement of the object being examined, for example tissue. Movement of the tissue being examined alters the value of the phase shift and has the effect of bringing back the terms for the sign of OPD (i.e. positive or negative) which otherwise would have been cancelled by the phase shifting method.

The paper entitled "Theoretical Study of Talbot-like Bands Observed Using a Laser Diode Below Threshold", by A. Gh. Podoleanu, S. Taplin, D. J. Webb and D. A. Jackson, published in J. Pure and Applied Optics, Vol. 7, (1998), pp. 517-536 and "Talbot-like Bands for Laser Diode Below Threshold", by A. Gh. Podoleanu, S. Taplin, D. J. Webb, D. A. Jackson, published in J. Pure and Applied Optics, vol. 6, issue 3, (1997), pp. 413-424, both report about Talbot bands using laser diodes below threshold levels. The latter paper also introduces a modified Michelson interferometer and such an apparatus will now be described with reference to FIG. 2.

FIG. 2 shows a similar arrangement to FIG. 1, but with the addition of two screens 20 placed in the optical paths 41 and 42. The two screens are arranged to block out half the diameter of the optical beams 41 and 42. Explanation of operation of the set-up in FIG. 2 will be provided for the case when the dispersing means 7 is a diffraction grating.

Consider the situation in which the beam reaching the diffraction grating 7 covers N grating lines. By introducing two screens 20, halfway through into the two optical paths, spatial separation of the two beams 41' and 42' occurs. The beams 41' and 42' are what is left out of the beams 41 and 42 after passing through the beam-splitter 4.

Usually, for maximum visibility of the interference result, those skilled in the art of interferometry understand that the height of the object beam 41 has to be adjusted to be at the same height as the reference beam 42. This can be achieved by conveniently tilting the beamsplitter 4, mirrors 5 and 6, to cause the beams 41 and 42 after reflection on mirrors 5 and 6 to be at the same height with the incoming beam 3. The beams 3, 41 and 42 are in the plane of the drawing. After introducing the two screens 20 into the two optical paths, the resulting beams 41' and 42' are parallel and relatively displaced in a displacing plane which in this particular case is identical with the drawing plane. The line connecting the centres of the two displaced beams 41' and 42' drawn in a direction perpendicular to the two beams is perpendicular to the grating lines.

The election in OPD can be explained by considering the two beams output of the interferometer as comprising a number of wavelets equal to the number of grating lines excited. In the arrangement shown in FIG. 2, the screens 20 are introduced halfway through the diameter of the beam and N/2 lines are excited instead of N lines corresponding to the whole beam diameter, therefore each wave-train comprises N/2 wavelets. As consequence of the Bragg grating equation applied for the first diffraction maximum, there is a delay of $\lambda$ between each wavelet and its neighbour in the wave-train. This means that each wave-train is $N\lambda/2$ long. Due to the action of the two screens 20, the two beams 41' and 42' are laterally displaced by a half-diameter of the initial beam. In the same way there is a delay of $\lambda$ due to the Bragg equation from a grating line to the next grating line, there is an intrinsic initial delay of $N\lambda/2$ between the two wave-trains diffracted, because the half diameter covers N/2 grating lines. Therefore, for the condition that the OPD is zero in the interferometer, the two wave-trains of length $N\lambda/2$ after diffraction incur an intrinsic delay of $N\lambda/2$. This means that their overlap is zero, which results in the channelled spectrum visibility being zero. By increasing the OPD in the interferometer, the wave-trains will overlap which results in a channelled spectrum. The minimum measurable OPD is the coherence length of the source, $L_C$, when at least two peaks are generated in the channelled spectrum. The overlap of the two wave-trains is maximum when the OPD in the interferometer equals $N\lambda/2$, i.e. when the wave-trains are delayed by $N\lambda/2$. In other words, the OPD in the interferometer has totally compensated for the intrinsic delay. It will readily be apparent to those skilled in the art that the overlap of the wave-trains reduces again when the OPD in the interferometer is larger, with the overlap reduced to zero when the wave-trains are delayed by their length in top of the intrinsic delay, i.e. for a total delay of $N\lambda$ which gives the maximum OPD range.

The OPD created in the interferometer is not sufficient in order to explain behaviour of the apparatus in FIG. 2. The OPD created in the interferometer combines with the intrinsic delay between the two laterally displaced beams, $N\lambda/2$, however, the channelled spectrum periodicity corresponds to the OPD in the interferometer only.

As explained in Podoleanu's papers mentioned above, delaying the two sides of the beam propagating to the grating results in a channelled spectrum when the OPD in the interferometer has a particular sign only. These papers make distinction between two cases, designated as L and R.

In the L case, the angles at which the diffraction grating 7 is used and the position of the screens 20 are such that the component of the reference beam 42' after diffraction is delayed by $N\lambda/2$ behind the wave left from the object beam 41' after diffraction. This means that an OPD in the Michelson interferometer produces a channelled spectrum and modulation of the CCD photodetector signal as long as it is between zero and $N\lambda$.

In the R case, the angles at which the diffraction grating is used and the position of the screens are such that the wavetrain of the beam 41' after diffraction is delayed by an intrinsic delay $N\lambda/2$ behind the wavetrain of the beam 42' after diffraction. This means that an OPD in the Michelson interferometer produces modulation of the CCD photodetector spectrum as long as it is between zero and −Nλ.

If the screens 20 are introduced into the beams 41 and 42 from the other side, then the beams 41' and 42' change their position after the beam-splitter 4 and the behaviour of the system changes from the case R to L and vice versa.

Similar explanations can be provided for other orders of diffraction or for a prism based spectral analysing element. In fact, the Talbot bands have been observed using a prism. When using the prism, the two incident beams are parallel and in a plane defined by the normal to the incident surface and the prism bisectrix. The fans of dispersed rays from both beams are contained in the same plane, defined by the normal to the exit surface and the prism bisectrix.

This is the key element in implementing a spectral OCT which can produce correct A-scans even if the origin of OPD in the interferometer is within the tissue. This is also the key element in selecting sensors in a multiplexed array by spectral low coherence interferometry, depending on the OPD corresponding to each sensor. However, the implementation described in the Podoleanu's papers above reduces the power of the signal two times in each beam due to the presence of the screens. Secondly, the low coherence sources are very sensitive to optical feedback and the Michelson interferometer returns light back to the source. Thirdly, the method of modifying the wave-train lengths in the two beams using the screens is inefficient, and the power is dependent on the position of the screens. Furthermore, the disclosure of the two Podoleanu's papers was restricted to the simplification of the spectral terms encountered in the Fourier transform of the channelled spectrum when a cavity low coherence source was used.

SUMMARY OF THE INVENTION

The object of the invention is to provide a spectral interferometry method and apparatus that obviates or ameliorates the above described problems associated with conventional means.

In general terms in a first aspect there is provided a spectral interferometry apparatus which comprises or is excited by an optical source. The optical source is arranged to provide two beams, an object beam which interacts with an object, and a reference beam arranged to have a path length of the order of the object beam path in order to elicit the interference effect to a workable extent. There may be some differences in the path lengths (optical path difference) especially in multi-layer objects with scattering points at different depths. Also the optical path difference may be purposely adjusted for various applications. The object and the reference beams are incident upon an optical spectrum dispersing means such as a diffraction grating or prism or some other device arranged to separate their spectral content. The object and reference beams are displaced laterally with respect to their paths such that they are incident on different parts of the dispersing means surface which is arranged at an angle to their respective paths in order to provide spectral dispersion. Thus any optical path difference together with the "intrinsic" path difference introduced by the angled dispersing surface will generate a channelled spectrum from the activity of the dispersing means.

The apparatus is arranged such that substantially the full power of the optical source is guided along the object beam path and the reference beam path. This can be achieved for example by avoiding the use of screens inserted to partially block the beams, and replace these for example with reflecting mirrors, focusing lenses, deflectors such as acoustic deflectors, refracting devices, fiber optic cable guidance arrangements, or a combination of these. By avoiding partial blocking of the beams, improved efficiency can be accomplished.

In particular in a first aspect the present invention provides a spectral interferometry apparatus, comprising an interferometer adapted to be excited by an optical source, the apparatus comprising: an optical arrangement arranged to guide an object beam from the optical source to an optical spectrum dispersing means, the object beam arranged in use to interact with a target object before being incident on the dispersing means; the optical arrangement further arranged to guide a reference beam from the optical source to the dispersing means; said beams having nominally equivalent path lengths but the arrangement being operable to introduce a relatively small optical path difference between the object beam and the reference beam; the optical spectrum dispersing means arranged to disperse the spectral contents of the respective beams incident thereon onto a reading element; the optical arrangement comprising separating means arranged to guide the object beam and the reference beam such that they are not co-terminous upon the dispersing means, wherein the separating means does not comprise screens to partially block the object and/or reference beams; wherein in use the combination of the separating means and the optical spectrum dispersing means is arranged to create an intrinsic optical delay between the wavetrains of the object beam and the reference beam; and wherein in use the optical path difference combined with the intrinsic optical delay generates a channelled spectrum on the reading element.

Preferably the separating means is arranged to perform one of the following optical actions on the object and/or reference beams in order to separate them: reflect; deflect; diffract; guide separately by means of fiber optic cable.

When used for spectral optical coherence tomography, the method and apparatuses according to the invention provide cross section images free of mirror terms in one measurement step.

According to a second aspect of the invention, there is provided a spectral interferometry apparatus, comprising an interferometer adapted to be excited by an optical source, the said interferometer comprising: object optics arranged to transfer a beam from the optical source to a target object to produce an object beam; reference optics arranged to produce a reference beam; displacing means arranged to displace at least one of the object beam and the reference beam to produce a relatively displaced object beam and a relatively displaced reference beam; wherein there is an optical path difference between the relatively displaced object beam and the relatively displaced reference beam generated in the interferometer; and optical spectrum dispersing means arranged to receive the two relatively displaced beams, and to disperse their spectral content onto a reading element; wherein in use the combination of the displacing means and the optical spectrum dispersing means is arranged to create an intrinsic optical delay between the wavetrains of the two relatively displaced object beam and the relatively displaced reference beam which can be used with the optical path difference in the interferometer to generate a channelled spectrum for the optical path difference in the interferometer on the reading element; and wherein the displacing means is adapted to relatively displace the object beam and the reference beam to produce the relatively displaced object beam and the relatively displaced reference beam using one or a combination of reflection, deflection, or refraction of at least one of the object beam and the reference beam.

Such an interferometry apparatus provides an efficient means for displacing the object beam and the reference beam. In embodiments of the present invention the displacement can performed by any combination of reflection, deflection and refraction. Hence, the displacement does not reduce the power of the object and reference beams.

The displacing means could introduce the relative displacement between the relatively displaced object beam and the relatively displaced reference beam by displacing either the object beam or the reference beam, or both. If the only the object beam is displaced, then the relatively displaced reference beam could be the same as the unaltered reference beam. Similarly, if the only the reference beam is displaced, then the relatively displaced object beam could be the same beam as the object beam.

Therefore, it will be understood that the use of the terms "relatively displaced object beam" and "relatively displaced reference beam" does not exclude apparatuses in which only one of the object or reference beam is displaced.

The displacing means may comprise at least two reflective elements, one of said at least two reflective elements being arranged to reflect the object beam and another of said at least two reflective elements being arranged to reflect the reference beam.

The displacing means may comprise at least one acoustic-optic modulator that is capable of deflecting beams.

According to a third aspect of the invention, there is provided a spectral interferometry apparatus, comprising an interferometer adapted to be excited by an optical source, the said interferometer comprising: object optics arranged to transfer a beam from the optical source to a target object to produce an object beam; reference optics arranged to produce a reference beam; displacing means arranged to displace at least one of the object beam and the reference beam to produce a relatively displaced object beam and a relatively displaced reference beam; wherein there is an optical path difference between the relatively displaced object beam and the relatively displaced reference beam generated in the interferometer; and optical spectrum dispersing means arranged to receive the two relatively displaced beams, and to disperse their spectral content onto a reading element; wherein in use the combination of the displacing means and the optical spectrum dispersing means is arranged to create an intrinsic optical delay between the wavetrains of the two relatively displaced object beam and the relatively displaced reference beam which can be used with the optical path difference in the interferometer to generate a channelled spectrum for the optical path difference in the interferometer on the reading element; and wherein the object optics includes object fiber optics comprising an object fiber end arranged to transmit the object beam and the reference optics includes reference fiber optics comprising a reference fiber end arranged to transmit the reference beam and the displacing means is arranged to move the relative positions of the object fiber end and the reference fiber end in order to produce the relatively displaced object beam and the relatively displaced reference beam.

The displacing means may further be arranged to produce the relatively displaced object beam and the relatively displaced reference beam by a combination of moving the relative positions of the object fiber end and the reference fiber end and any one or combination of reflection, deflection, and refraction.

According to a fourth aspect of the invention, there is provided a spectral interferometry apparatus, comprising an interferometer adapted to be excited by an optical source, the said interferometer comprising: object optics arranged to transfer a beam from the optical source to a target object to produce an object beam; reference optics arranged to produce a reference beam; displacing means arranged to displace at least one of the object beam and the reference beam to produce a relatively displaced object beam and a relatively displaced reference beam; wherein there is an optical path difference between the relatively displaced object beam and the relatively displaced reference beam generated in the interferometer; and optical spectrum dispersing means arranged to receive the two relatively displaced beams, and to disperse their spectral content onto a reading element; wherein in use the combination of the displacing means and the optical spectrum dispersing means is arranged to create an intrinsic optical delay between the wavetrains of the two relatively displaced object beam and the relatively displaced reference beam which can be used with the optical path difference in the interferometer to generate a channelled spectrum for the optical path difference in the interferometer on the reading element; and wherein one of the object optics or the reference optics includes fiber optics comprising a fiber end arranged to transmit a respective one of the object beam or the reference beam, and the displacing means is arranged to produce the relatively displaced object beam and the relatively displaced reference beam by movement of the fiber end.

The displacing means may be further arranged to produce the relatively displaced object beam and the relatively displaced reference beam by a combination of moving the fiber end and any one or combination of reflection, deflection, and refraction.

In some embodiments, the displacing means is adapted to alter the diameters of at least one of the object beam and the reference beam.

In some embodiments, means arranged to control the optical path difference in the interferometer may be provided. Means arranged to control the intrinsic optical delay between the relatively displaced object beam and the relatively displaced reference beam may also be provided. The means arranged to control the optical path difference and the intrinsic optical delay may comprise processing means.

The reading element may be arranged to provide a signal to a signal analyser, the signal analyser being arranged to determine the distribution of reflections or scattering points in a depth range within the target object. The apparatus may be arranged to adjust the depth range by adjusting the diameter of at least one of the relatively displaced object beam and the relatively displaced reference beam.

Means to match the polarization of the relatively displaced object and the relatively displaced reference beam with that of the optical dispersing means may also be provided.

In some embodiments, means to compensate for dispersion in the interferometer may also be provided.

The displacing means may adapted to relatively orient the relatively displaced object beam and the relatively displaced reference beam in a displacement plane. The displacing means may adapted to permit adjustment of the relatively displaced object beam and the relatively displaced reference beam until they become parallel in the displacement plane.

The displacement means may be arranged to permit an adjustable lateral superposition of the two relatively displaced beams in the displacement plane onto the optical spectrum dispersing means in order to enhance the strength of the signal for small optical path difference values, wherein the lateral superposition is from partial superposition to a total overlap.

The displacing means may be adapted to relatively orient the relatively displaced object beam and the relatively displaced reference beam such that they hit different portions of the optical spectrum dispersing means.

The optical spectrum dispersing means may comprise any one of or combination of: a diffraction grating, a prism; a group of prisms; a group of diffraction gratings.

The optical spectrum dispersing means may comprise a diffraction grating, wherein grating lines of the diffraction grating are perpendicular to a line connecting the centre of the relatively displaced reference beam and the centre of the relatively displaced object beam.

The optical spectrum dispersing means may comprise a prism including an entrance surface, wherein a line connecting the centre of the relatively displaced reference beam and the centre of the displaced object beam, is within the plane defined by the normal to the entrance surface of this prism and its bisectrix.

The reference optics may comprise at least one reflector arranged to provide a reference light source by reflecting a beam of the optical source, wherein the position or tilt of the reflector can be adjusted in order to control the optical path difference of the relatively displaced object beam and the relatively displaced reference beam.

The reference optics may be arranged to transfer an optical beam from the optical source to the displacing means along via fiber optics or via reflectors arranged to prevent light form being sent back to the optical source.

The object optics comprises a first zoom element arranged to alter the diameter of the object beam. A third zoom element may be provided to alter the diameter of the relatively displaced object beam.

The reference optics may comprise a second zoom element arranged to alter the diameter of the reference beam. A fourth zoom element may be provided to alter the diameter of the relatively displaced reference beam.

The displacement means may be arranged to create an adjustable gap between the two relatively displaced beams in order to adjust the minimum optical path difference value for which a modulation of the optical spectrum could be sensed at the reading element.

By allowing some overlap of the two laterally displaced beams, the signal for small OPD values is enhanced. This may be desired in those cases where the OPD=0 position could be placed within the multi-layer object and there is a lack of scattering points on one side of the OPD=0 depth.

The interference between the two relatively displaced beams in the interferometer may take place entirely on the said reading element.

The interference between the two relatively displaced beams is arranged to take place partially on the said reading element and partially on the said optical spectrum dispersing means.

The displacing means may be arranged to adjust the amount of lateral superposition of the said displaced beams in order to enhance the strength of the signal for small optical path difference values.

The processing means may be arranged to control the displacing means in order to adjust the gap between the relatively displaced object beam and the relatively displaced reference beam in order to alter the minimum optical path difference value for which a modulation of the optical spectrum could be sensed at the reading element.

The object optics may comprise a scanning element, the scanning element being arranged to scan the target object. The scanning element may be arranged to perform any one of combination of: linear scanning; raster scanning; elicoidal scanning; circular scanning; or any other random shaped scanning.

The scanning element can be used to obtain cross section images from the inside of the object which are free of the mirror terms. By repeating the acquisition of cross sections at different transverse positions, several cross sections from inside the object can be acquired which subsequently, by software means are used to reconstruct a 3D volume of the object free of mirror terms.

Focusing elements may be provided in the object optics to enhance the signal strength from a particular depth within the object.

The interferometer may comprise an in-fiber or a bulk interferometer or a hybrid interferometer of in-fiber and bulk components.

The said optical source may be a low coherence source.

The reading element may comprise: a photodetector array; a CCD linear array; a two dimensional array of photodetectors; a two dimensional CCD array; or a point photodetector over which the dispersed spectrum is scanned.

In some embodiments, the apparatus further comprises: beam splitting means arranged to receive the object beam and the reference beam and to produce a second object beam and a second reference beam; second displacing means arranged to displace at least one of the second object beam and the second reference beam to produce a second relatively displaced object beam and a second relatively displaced reference beam, second optical spectrum dispersing means arranged to receive the second relatively displaced object beam and the second relatively displaced reference beam, and to disperse their spectral content onto a second reading element; wherein in use the combination of the second displacing means and the second optical spectrum dispersing means is arranged to create a second intrinsic optical delay between the wavetrains of the second relatively displaced object beam and the second relatively displaced reference beam which can be used with the optical path difference in the interferometer to generate a channelled spectrum for the optical path difference in the interferometer on the second reading element.

The second displacing means may be adapted to produce the second relatively displaced object beam and the second relatively displaced reference beam by using one or a combination of reflection, deflection and refraction of at least one of the second object beam and the second reference beam.

The optical spectrum dispersing means and the second optical dispersing means may be oriented in such way that in combination with their respective relatively displaced object beam and relatively displaced reference beam, the spectrally dispersed beams from the optical spectrum dispersing means and the second optical dispersing means exhibit intrinsic delays of opposite sign.

The second reading element may be arranged to provide a signal to a second signal analyser, and apparatus may provide a profile of reflectivity versus optical path difference for the target object covering both signs of optical path difference values on the basis of signals output from the signal analyser and the second signal analyser.

The second optical dispersing means may comprise a diffraction grating or gratings, the diffraction grating or gratings being arranged to diffract orders of opposite sign to the said reading element and the said second reading element.

The optical dispersing means and the second optical dispersing means may each comprise one or more prisms, the one or more prisms being arranged such that the relatively displaced object beam or the relatively displaced reference beam is closest to prism apex in the optical dispersing means and the second relatively displaced reference beam or the second relatively displaced object beam respectively is closest to the prism apex in the second optical dispersing means.

In some embodiments, a signal output of each of the reading element and the second reading element is sent to a separate frequency to amplitude converter, and the apparatus is arranged such that the output of one frequency to amplitude converter is summed to an inverted output of the other frequency to amplitude converter in order to provide a signal strength proportional to the axial position of a single layer object irrespective of the OPD sign.

In some embodiments, the apparatus further comprises: third beam splitting means arranged between the displacing means and the optical spectrum dispersing means, the beam splitting means being arranged to receive the relatively displaced object beam and the relatively displaced reference beam to produce a third relatively displaced object beam and a third relatively displaced reference beam; third displacing means arranged to adjust the relative displacement of at least one of the third relatively displaced object beam and the third relatively displaced reference beam; third optical spectrum dispersing means arranged to receive the third relatively displaced object beam and the third relatively displaced reference beam, and to disperse their spectral content onto a second reading element; wherein in use the combination of the third displacing means and the third optical spectrum dispersing means is arranged to create a third intrinsic optical delay between the wavetrains of the third relatively displaced object beam and the third relatively displaced reference beam which can be used with the optical path difference in the interferometer to generate a channelled spectrum for the optical path difference in the interferometer on the third reading element.

The third displacing means may be adapted to adjust the relative displacement of at least one of the third relatively displaced object beam and the third relatively displaced reference beam using one or a combination of reflection, deflection and refraction of at least one of the third relatively displaced object beam and the third relatively displaced reference beam.

For a sufficiently large gap between two displaced beams, a maximum of sensitivity is registered for a certain optical path difference in the interferometer within the depth interval range which corresponds to a depth value, $d_M$ in the object. Focussing elements may be adjusted to create a focus which: i) coincides with $d_M$, in order to create a narrow profile of the sensitivity versus optical path difference in the interferometer and depth in the object; ii) differs from $d_M$, in order to flatten the profile of the sensitivity versus optical path difference in the interferometer and depth in the object.

The source may be a low coherence source the output of which is send with a delayed replica by means of an optical duplicating element.

For an object to be investigated having a thickness less than half of the depth range of the apparatus, the output of the low coherence source may sent to the spectral interferometry apparatus together with a delayed replica, via an optical duplicating element, which generates a differential delay smaller than the maximum optical path range to which the apparatus is sensitive, or preferably, close to middle of this range.

The gap between the two displaced beams may be adjusted larger than the sum of their radiuses, in order to make the apparatus sensitive to the depth range of OPD sign to which the apparatus was insensitive before the introduction of the differential delay, and the OPD values rejected without the differential delay appear in the range interval (Maximum depth range of the apparatus minus the differential delay—Maximum depth range of the apparatus).

The optical duplicating element may comprise a first single mode coupler whose outputs are connected to two inputs of a second single mode coupler in order to create the delayed replica of the optical source. This may create a delayed replica of the optical source delayed by the differential delay between the two leads connecting the first and the second single mode coupler.

The optical duplicating element may comprise a transparent optical material in the form of a plate with parallel surfaces, which is introduced halfway through into the beam of the optical source in such a way that its edge is parallel to the displacement plane.

The source may be a low coherence source comprising a laser driven below threshold.

The cavity length may be smaller than the maximum optical path range to which the apparatus is sensitive, or preferably, close to middle of this range. When the gap between the two displaced beams is adjusted larger than the sum of their radiuses, the apparatus is sensitive to the depth range of OPD sign to which the apparatus would be insensitive if a non-cavity low coherence source was used. The OPD values rejected when using a non-cavity low coherence source appear in the range interval (Maximum depth range of the apparatus minus the optical laser cavity length-Maximum depth range of the apparatus).

The optical source may a non-cavity source exhibiting satellite peaks in the autocorrelation function, and the differential delay value according may match the value of the OPD of the first satellite peak.

Polarisation modulators and waveplates may be used in the object and reference beams or in the said displaced object and reference beams to provide polarisation sensitive tomograms, free of mirror terms.

According to a fifth aspect of the invention, there is provided a spectral interferometry method, comprising: using an interferometer to output an object beam and a reference beam; reflecting, deflecting or refracting at least one of said object beam and said reference beam in order to relatively displace at least one of the object beam and the reference beam to produce a relatively displaced object beam and a relatively displaced reference beam, wherein there is an optical path difference between the relatively displaced object beam and the relatively displaced reference beam generated in the interferometer; dispersing the two relatively displaced beams according to their optical spectral content onto a reading element using an optical spectrum dispersing means; wherein the combination of reflecting, refracting or refracting said object beam and said reference beam to produce a relatively displaced object beam and a relatively displaced reference beam and dispersing the two relatively displaced beams using a optical spectrum dispersing means leads to an intrinsic optical delay between the wavetrains in the two relatively displaced beams which can be used with the optical path difference in the interferometer to generate a channelled spectrum for the optical path difference in the interferometer.

According to a sixth aspect of the invention, there is provided a spectral interferometry method, comprising an interferometer adapted to be excited by an optical source, the said interferometer comprising object optics and reference optics, the method comprising: using the object optics to transfer a beam from the optical source to a target object to produce an object beam; using reference optics to produce a reference beam; using displacing means to displace at least one of the object beam and the reference beam to produce a relatively displaced object beam and a relatively displaced reference beam; wherein there is an optical path difference between the relatively displaced object beam and the relatively displaced reference beam generated in the interferometer; and using optical spectrum dispersing means to receive the two relatively displaced beams, and to disperse their spectral content onto a reading element; wherein the combination of the displacing means and the optical spectrum dispersing means is arranged to create an intrinsic optical delay between the wavetrains of the two relatively displaced object beam and the relatively displaced reference beam which can be used with the optical path difference in the interferometer to generate a channelled spectrum for the optical path difference in the interferometer on the reading element; and wherein the displacing means relatively displaces the object beam and the reference beam to produce the relatively displaced object beam and the relatively displaced reference beam using one or a combination of reflection, deflection, or refraction of at least one of the object beam and the reference beam.

According to a seventh aspect of the invention, there is provided a spectral interferometry method, comprising using an interferometer adapted to be excited by an optical source, the said interferometer including object optics and reference optics, the method comprising: using the object to transfer a beam from the optical source to a target object to produce an object beam; using reference optics to produce a reference beam; using displacing means to displace at least one of the object beam and the reference beam to produce a relatively displaced object beam and a relatively displaced reference beam; wherein there is an optical path difference between the relatively displaced object beam and the relatively displaced reference beam generated in the interferometer; and optical spectrum dispersing means arranged to receive the two relatively displaced beams, and to disperse their spectral content onto a reading element; wherein the combination of the displacing means and the optical spectrum dispersing means is arranged to create an intrinsic optical delay between the wavetrains of the two relatively displaced object beam and the relatively displaced reference beam which can be used with the optical path difference in the interferometer to generate a channelled spectrum for the optical path difference in the interferometer on the reading element; and wherein the object optics includes object fiber optics comprising an object fiber end arranged to transmit the object beam and the reference optics includes reference fiber optics comprising a reference fiber end arranged to transmit the reference beam and the displacing means moves the relative positions of the object fiber end and the reference fiber end in order to produce the relatively displaced object beam and the relatively displaced reference beam.

According to an eighth aspect of the invention, there is provided a spectral interferometry method, comprising using an interferometer adapted to be excited by an optical source, the said interferometer including object optics and reference optics, the method comprising: using object optics to transfer a beam from the optical source to a target object to produce an object beam; using reference optics to produce a reference beam; using displacing means to displace at least one of the object beam and the reference beam to produce a relatively displaced object beam and a relatively displaced reference beam; wherein there is an optical path difference between the relatively displaced object beam and the relatively displaced reference beam generated in the interferometer; and using optical spectrum dispersing means to receive the two relatively displaced beams, and to disperse their spectral content onto a reading element; wherein in use the combination of the displacing means and the optical spectrum dispersing means is arranged to create an intrinsic optical delay between the wavetrains of the two relatively displaced object beam and the relatively displaced reference beam which can be used with the optical path difference in the interferometer to generate a channelled spectrum for the optical path difference in the interferometer on the reading element; and wherein one of the object optics or the reference optics includes fiber optics comprising a fiber end arranged to transmit a respective one of the object beam or the reference beam, and the displacing means produces the relatively displaced object beam and the relatively displaced reference beam by movement of the fiber end. and partially on the said optical spectrum dispersing means.

The method may comprise using beam splitting means to receive the object beam and the reference beam and to produce a second object beam and a second reference beam; using second displacing means arranged to displace at least one of the second object beam and the second reference beam to produce a second relatively displaced object beam and a second relatively displaced reference beam, using second optical spectrum dispersing means arranged to receive the second relatively displaced object beam and the second relatively displaced reference beam, and to disperse their spectral content onto a second reading element; wherein in use the combination of the second displacing means and the second optical spectrum dispersing means creates a second intrinsic optical delay between the wavetrains of the second relatively displaced object beam and the second relatively displaced reference beam which can be used with the optical path difference in the interferometer to generate a channelled spectrum for the optical path difference in the interferometer on the second reading element.

The second displacing means may produce the second relatively displaced object beam and the second relatively displaced reference beam by using one or a combination of reflection, deflection and refraction of at least one of the second object beam and the second reference beam.

The method may comprise orienting the optical spectrum dispersing means and the second optical dispersing means in such way that in combination with their respective relatively displaced object beam and relatively displaced reference beam, the spectrally dispersed beams from the optical spectrum dispersing means and the second optical spectrum dispersing means exhibit intrinsic delays of opposite sign.

The second reading element may provide a signal to a second signal analyser, and the method further comprise providing a profile of reflectivity versus optical path difference for the target object covering both signs of optical path difference values on the basis of signals output from the signal analyser and the second signal analyser.

A signal output of each of the reading element and the second reading element may be sent to a separate frequency to amplitude converter, the apparatus being arranged such that the output of one frequency to amplitude converter is summed to an inverted output of the other frequency to amplitude converter in order to provide a signal strength proportional to the axial position of a single layer object irrespective of the OPD sign.

The method may comprise using third beam splitting means arranged between the displacing means and the optical spectrum dispersing means to receive the relatively displaced object beam and the relatively displaced reference beam and to produce a third relatively displaced object beam and a third relatively displaced reference beam; using third displacing means to adjust the relative displacement of at least one of the third relatively displaced object beam and the third relatively displaced reference beam; using third optical spectrum dispersing means to receive the third relatively displaced object beam and the third relatively displaced reference beam, and to disperse their spectral content onto a second reading element; wherein in use the combination of the third displacing means and the third optical spectrum dispersing means is creates a third intrinsic optical delay between the wavetrains of the third relatively displaced object beam and the third relatively displaced reference beam which can be used with the optical path difference in the interferometer to generate a channelled spectrum for the optical path difference in the interferometer on the third reading element.

The third displacing means may adjust the relative displacement of at least one of the third relatively displaced object beam and the third relatively displaced reference beam using one or a combination of reflection, deflection and refraction of at least one of the third relatively displaced object beam and the third relatively displaced reference beam.

The method may further comprise arranging the signal analyser and the second signal analyser (or third signal analyser) in such a way that only two main peaks are retained in total in the accumulated signal output of the signal analyser and the second signal analyser (or third signal analyser), and determining the thickness of the object on the basis of the difference between the maximum and minimum frequency of the two peaks arising at the output of one of the signal analyser and the second signal analyser (or third signal analyser) when no other signal exceeds a threshold at the output of the other of the signal analyser and the second signal analyser (or third signal analyser).

The method may further comprise arranging the signal analyser and the second signal analyser (or third signal analyser) in such a way that only two main peaks are retained in total in the accumulated signal output of the signal analyser and the second signal analyser (or third signal analyser), and determining the thickness of the object on the basis of the sum of the extreme frequencies of the signal analyser and the second signal analyser (or third signal analyser) when the signal exceeds a threshold only once in the output of each of the signal analyser and the second signal analyser (or third signal analyser).

A thresh-holding circuit may be mounted at the output of each of the signal analyser and the second signal analyser (or third signal analyser) to discard non-essential peaks which represent noise and peaks from the target of smaller amplitudes in such a way that only two main peaks are retained in total in accumulated signal output of the signal analyser and the second signal analyser (or third signal analyser).

The novel features which are believed to be characteristic of the present invention, as to its structure, organization, use and method of operation, together with further objectives and advantages thereof, will be better understood from the following drawings in which presently preferred embodiments of the invention will now be illustrated by way of example.

It is expressly understood, however, that the drawings are for the purpose of illustration and description only and are not intended as a definition of the limits of the invention. Embodiments of this invention will now be described by way of example in association with the accompanying drawings in which:

DETAILED DESCRIPTION OF THE INVENTION

Components which are the same in the various figures have been designated by the same numerals for ease of understanding.

Where optical fibres are used, this is only as an example and it should be noted that a bulk implementation is equally feasible, in which case the respective elements using in-fiber components, are to be replaced by optical paths and the directional fiber couplers by plate beam-splitters. Likewise, where bulk components are used, they could equally be replaced by optical fiber components.

The novel features which are believed to be characteristic of the present invention, as to its structure, organization, use and method of operation, together with further objectives and advantages thereof, will be better understood from the following discussion.

Figure 3:
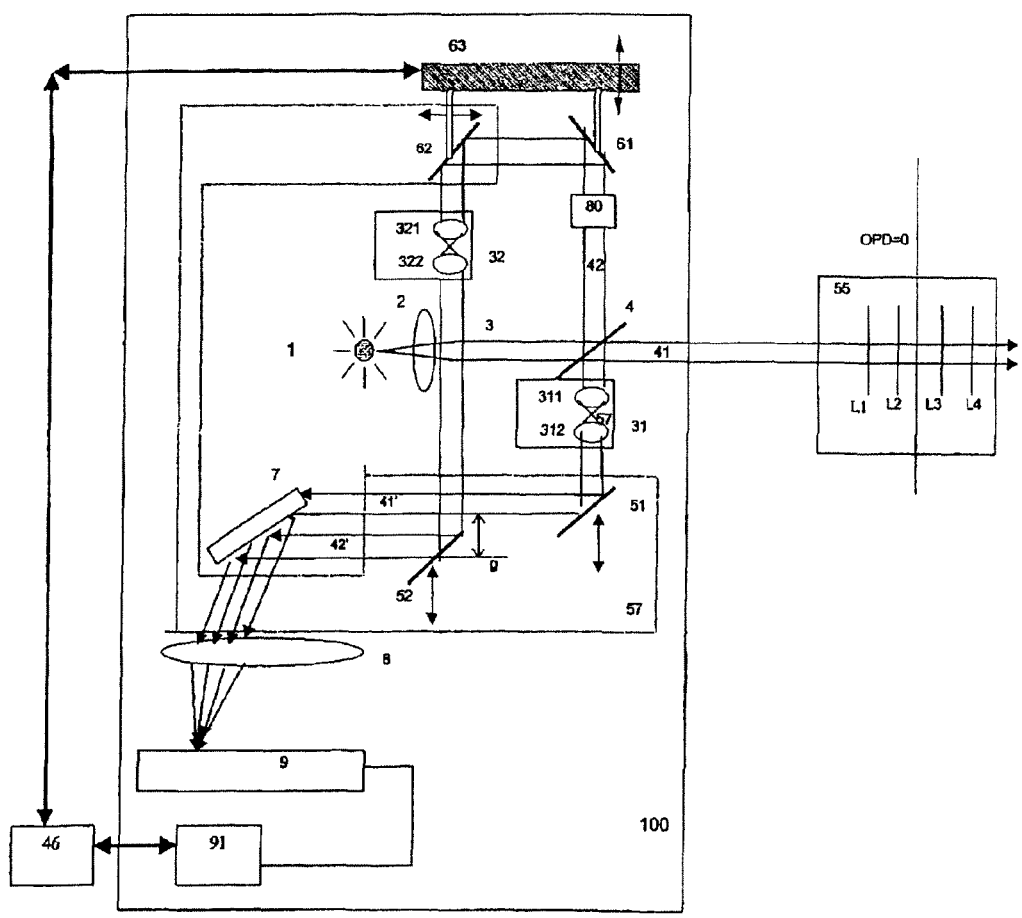
FIG. 3 shows a first version of the embodiment of an efficient optical configuration to be used in a spectral interferometry apparatus selective in OPD in order to deliver un-ambiguous A-scans in a multi-layered object.

FIG. 3 shows a spectral interferometry apparatus 100 according to a first embodiment of the present invention. The apparatus 100 is selective in OPD and is capable of generating unambiguous A-scans based on a white light interferometer. Different interferometer configurations can be envisaged to produce two beams, an object beam directed to the target and a reference beam. To avoid light being sent back to the source, a re-circulating reference beam configuration is illustrated in FIG. 3.

As opposed to prior art implementations of spectral (or Fourier domain) OCT, in which the two beams from the object and from the reference paths are spatially superposed on the spectral analysing element, in embodiments of the present invention the two beams are relatively displaced from each other on the spectral analysing element. In prior art arrangements, for example those described in papers by Hausler and U.S. Pat. No. 4,932,782, or 5,317,389 mentioned above, in the interference result is sent to the dispersing element, ie the interference has taken place before the dispersion (diffraction). In embodiments of the present invention, essentially the interference takes place after dispersion (diffraction).

The apparatus shown in FIG. 3 comprises a source 1, a collimating element 2 and a beam splitter 4. A first optical path 41 is defined in the apparatus that leads from the beam splitter 4 to a target object 55. A second optical path 42 is defined, in the apparatus that leads from the beam splitter 4 to a mirror 52 via two re-circulating mirrors 61 and 62, which are arranged on a translation stage 63. A third optical path is defined in the apparatus that leads from the beam splitter 4 to a mirror 51. A zoom element 32 is arranged in the second optical path, and a zoom element 31 is placed in the third optical path. Optical spectrum dispersing means for spectral analysis, 7 is arranged to receive optical beams that have been reflected from the second and third optical paths by the mirrors 52 and 51. The optical spectrum dispersing means 7 disperses the different wavelength components of the optical beams at different angles according to their wavelength, onto a reading element 9, via a focussing element 8. The reading element 9 provides an electrical output to a spectrum analyser 91. A processor 46 controls the parameters of the spectrum analyser 91 in terms of acquisition rate and bandwidth and processes its output signal while at the same time synchronously controls the position of the translation stage 63 and the mirrors 51 and 52.

In the apparatus of FIG. 3, an optical beam from the source 1 is collimated by the collimating element 2, to form an optical beam 3. In this embodiment the collimating element 2 is a simple lens, but in other embodiments it could be an achromat, or a mirror or combination of lenses or mirrors.

The light from the beam 3 is divided by the beam-splitter 4 into two beams, along a first optical path by object optics to form the object beam 41, and along a second optical path by reference optics to form the reference beam 42. On return from the target object 55, the object beam 41 is reflected by the beam-splitter 4 along the third optical path in the object optics. The object beam from the third optical path is reflected by the mirror 51 to produce a relatively displaced beam 41'. The reference beam 42 is reflected by the two mirrors 61 and 62 and then by the reflective element 52 to produce a relatively displaced beam 42'. In this embodiment, the combination of the re-circulating mirror 61 and the reflecting elements 51 and 52 act as displacing means, 57, as shown by the dashed block in FIG. 3.

The two beams 41' and 42' are relatively displaced from each other in the displacement plane, which could be identical with the plane of the drawings, in such a way to maintain the parallelism of beams 41' and 42', and such a displacement may exceed their beam diameter and a lateral gap g created between them. The two mirrors, 61 and 62 are arranged on the translation stage 63, which is used to adjust the OPD in the interferometer between the object beam path, formed by the round trip path length along the first path 41 and along the third path of the displaced object beam 41' up to the dispersing element 7, or up to the reading element 9 for no overlap of the displaced beams and the reference beam path formed by the length of the second path 42 and the length along the path of the displaced reference beam 42' up to the dispersing element 7, or up to the reading element 9 for no overlap of the displaced beams. The lateral gap g between the two beams 41' and 42' can be altered by moving either the mirror 51 or 62 or the mirror 52 in the direction shown by arrows. In other embodiments, the reflective element 52 could be a beam splitter or a combination of mirrors. If small values of the gap are required, approaching zero value, or when lateral superposition of the beams is required, then the reflective element 52 comprises a beam-splitter. By adjusting the amount of lateral superposition of the lateral gap, g, the intrinsic delay between the wavetrains in the two relatively displaced beams can be adjusted. If the second path via mirrors 61 and 62 is routed to the right in the figure, (by having 61 rotated by 90°)
and not to the left as shown in FIG. 3, then mirror 51 needs to be a beamsplitter. The zoom elements 31 and 32 are used to adjust the diameter of the beam falling on the optical spectrum dispersing element 7, and in this embodiment the zoom elements 31 and 31 comprise a set of two lenses 311 and 312 and 321 and 322 respectfully. By modifying the focal length of the lenses 312 and 322 in relation to the focal length of the lenses 311 and 321, the beam diameter falling on the element 7 can be de-magnified or magnified.

It should be noted that, for the purposes of this description, the terms "relatively displaced object beam" and "relatively displaced reference beam" will be used to refer to the respective directions of the object and reference beam that have been displaced relative to each other. However, it will be readily understood by those skilled in the art that the relative displacement could be introduced by displacing either the object beam or the reference beam, or both. Therefore, it will be understood that the use of the terms "relatively displaced object beam" and "relatively displaced reference beam" does not exclude apparatuses in which only one of the object or reference direction is displaced.

Furthermore, the object and reference beams in every embodiment could be displaced by deflectors suitably oriented, acoustic-optic modulators or by refractive elements introduced in one or both object and reference beams.

Here by way of example, the two beams are spatially displaced so as to fall on different portions of the dispersing means 7, while they are maintained parallel, for ease of description in relation to a simple dispersing element such as a diffraction grating. This however should not restrict the generality of displacing the two beams in relation to each other which in more complex spectral analysing elements may involve the two beams using the same part of the dispersing means but being incident at different angles, the effect of the relatively displacing the beams being the generation of an intrinsic differential delay between the two dispersed beams at the output of the dispersing means.

In this embodiment, the optical spectrum dispersing element 7 is a diffraction grating. Therefore, by varying the diameter of the two beams 41' and 42', $N_O$ grating lines are excited by the object beam 41' and $N_R$ grating lines by the reference beam 42'. Varying the beam diameters can also change. It is possible that by enlarging the beam diameters to completely annul the gap between the two initially displaced beams and even overlap the beams.

In order to maximize the interference and hence the visibility, polarization controller 80 is shown the reference optics and is used to match polarizations in the object and reference optics. Only one element, 80 is shown in FIG. 3, which may suffice for most of the practical situations. However, one or more polarization controllers can also be used in the object optics as well. The polarization controllers used in this embodiment are polarisers in bulk. However, in-fiber polarisers, or a wave-plate in bulk or in-fiber and any combination thereof can be used.

The light diffracted by the diffraction grating 7 is focused by a convergent lens 8 onto the reading element. In this embodiment the reading element is a CCD array 9. It is known in the art that for optimal operation, the lens 8 is placed at the distance F from the diffraction grating 7 and at the same distance F from the CCD array 9; where F is the focal length of the lens 8. Other spectral analysing set-ups could be used without diverting from the scope of the invention. For example, in other embodiments, the optical spectrum dispersing element 7 could comprise other dispersing means such as a prism, or a groups of prisms or diffraction gratings. Furthermore, in other embodiments, the CCD array 9 could be replaced by a photodetector array, or by a simple photodetector, in which case the diffracted or dispersed beam from the optical spectrum dispersing element 7 could be scanned over a point photodetector using an angular scanner such as a galvo-scanner, resonant scanner, polygon mirror or rotating prism. Any implementation could be used, that is operable to produce an electric signal which varies in time according to the shape of the compound spectrum resulting from the superposition of the dispersed fan of rays due to the relatively displaced beams 41' and 42'.

The signal output of the reading element is processed in an electronic processor to extract the A-scan profile from the periodicity of the modulation of the optical spectrum as read by the reading element 9. A-scan is the profile of reflectivity in depth. This is usually accomplished by Fourier transformation, however, other procedures can serve the same goal, such as Laplace, wavelet transformation, Hilbert transformation, etc, together with spectral smoothening using different shaped kernels, zero padding, interpolation to provide a linear scale in optical frequencies, iterative methods, etc, as known in the art of spectral analysis.

In this embodiment, the displacing means is controlled by the processor 46, which controls the adjustment of the positions of the re-circulating mirror 61, reflecting elements 51 and 52 and the zoom elements 31 and 32. However, in other embodiments, the displacing means could be adjusted manually, or by ant other suitable means.

In order to understand the operation of the embodiment in FIG. 3, an example will be described with reference to FIG. 4. In this example, the target object 55 in the arrangement shown in FIG. 3 is multi-layered, and comprises four layers: L1, L2, L3 and L4.

Figure 1:
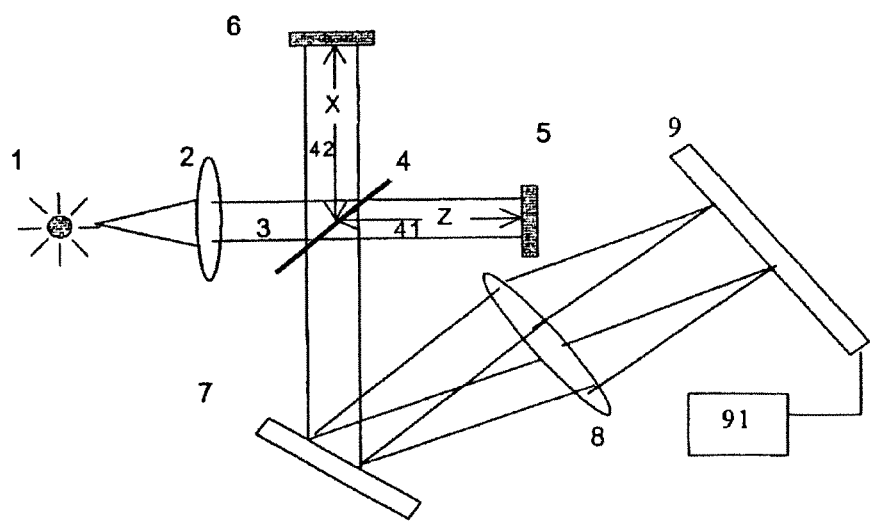
FIG. 1 shows prior art of a spectral OCT.
Figure 4:
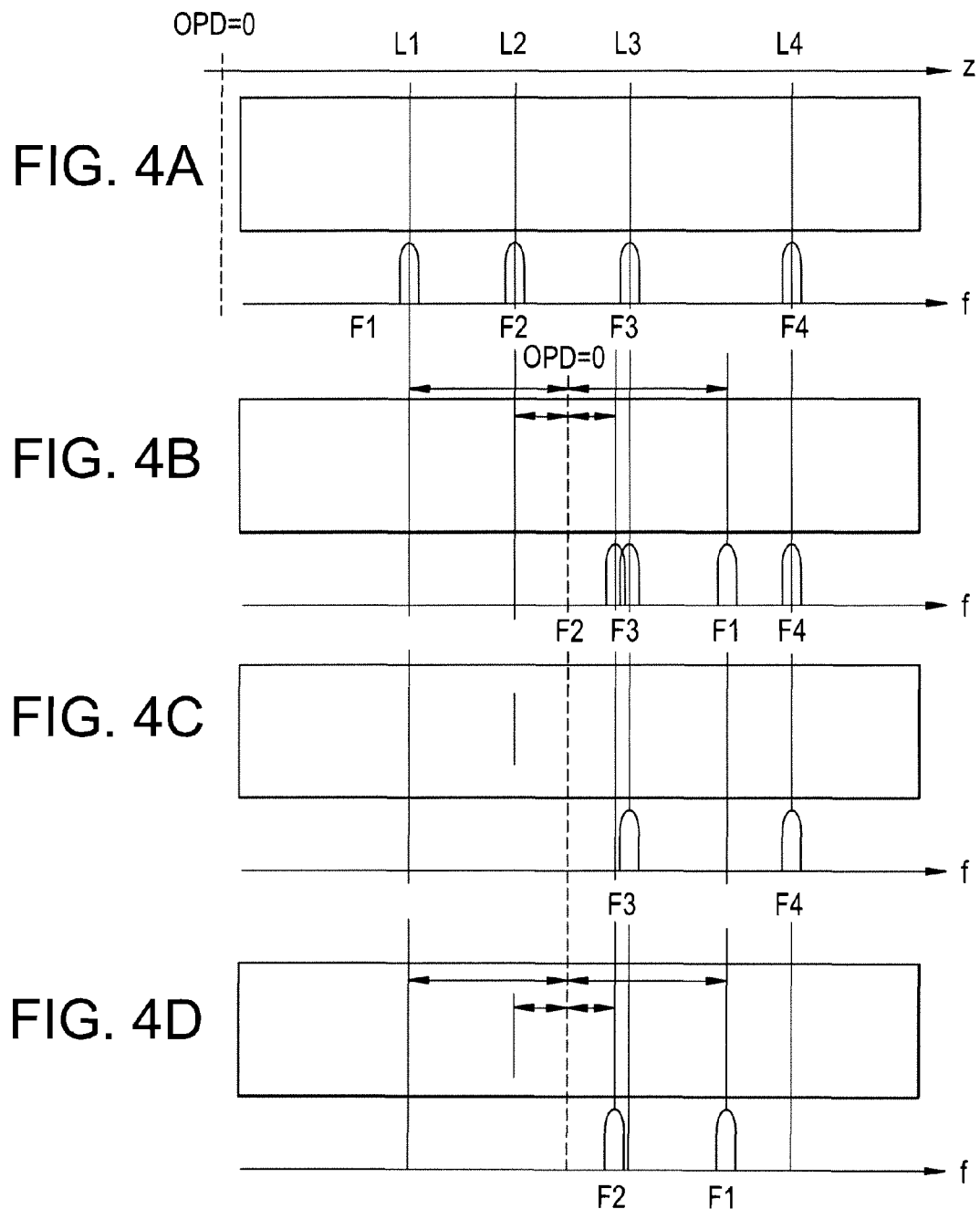
FIG. 4 shows a comparison of depth profiles delivered by the prior art apparatus shown in FIG. 1 and the embodiment of the invention shown in FIG. 3.

FIG. 4 shows comparatively, the depth profile delivered by the prior art method discussed above in relation to FIG. 1, and the method according to embodiments of the present invention. Different cases are illustrated, as shown by the output peaks, at frequencies F1, F2, F3 and F4 corresponding to the modulation of the channelled spectrum as measured by the electrical spectrum analyser 91, and each frequency is proportional to the OPD in the interferometer that corresponds to the depth of the layers L1 to L4 of the target object. The output peaks are denoted as their frequencies in the following description. Peaks F1 to F4 result by performing Fourier transformation of the optical spectrum using the spectrum analyser 91. The larger the OPD, the denser the channelled spectrum, and the higher the frequency F of the signal corresponding to that OPD. Peaks F1 to F4 are represented along the electrical frequency axis, f.

In case (a), the OPD=0 surface is in front of the multi-layered object. In cases (b), (c) and (d) the OPD=0 surface is within the multi-layered object. The position where OPD=0 is indicated by the dashed line. Such a position is determined by the position of the translation stage 63 in FIG. 3. In the cases (b), (c) and (d), the position at which the OPD is zero is adjusted between the OPD position matching the depth of the second layer L2 and the OPD position matching the third layer L3, slightly closer to the depth where the second layer is. Cases (c) and (d) correspond to the situation in which the OPD has a particular sign only, and correspond to the L and R cases discussed above in relation to FIG. 2.

In case (a), the prior art outputs a channelled spectrum whose Fourier spectrum has peaks at frequencies F1 to F4 whose positions resemble that of the layers L1 to L4 in depth. This corresponds to a correct detection of layers in depth and to correct tomograms (A-scans).

However, when the OPD=0 surface is inside the multi-layered object, the prior art method delivers incorrect results, as shown in FIG. 4 (b). In this case, the peaks F1 and F2 do not correspond to the depth of layers L1 and L2. Furthermore the peak F2 is almost superposed on the peak F3, being only slightly shifted towards the origin relative to F3. This slight shift being because the initial OPD=0 was closer to layer L2 than layer L3. Only the peaks F3 and F4 have correct positions.

FIG. 4b illustrates that for layer depths of OPD>0, i.e. when the object path is longer than the reference path, correct detection of the peaks will occur. However, incorrect detection will occur for layer depths when OPD<0.

If embodiments of the invention described in relation to FIG. 3 are employed, then the signal as described in FIG. 4 (c) results. In this case, only the peaks F3 and F4 are obtained and peaks F1 and F2 are eliminated. In other words, all layers situated at OPD<0 are eliminated from the spectrum, leaving a clean output with strict resemblance of the multi-layered structure in depth for OPD>0. It will be apparent that, if the two relatively displaced beams 41' and 42' directed to the diffraction grating are swooped or if the grating rotated in such a way that the diagram corresponds to the case R as described in the two Podoleanu's papers mentioned above, then pulses F1 and F2 will correctly display the depth position of layers L1 and respectively L2, while the pulses F3 and F4 will be eliminated, as shown in FIG. 4 (d). The same explanation will apply if OPD in the interferometer is defined by deducting the object path from the reference path, and the initial OPD between the two beams incident on the diffraction grating is suitably defined.

Figure 2:
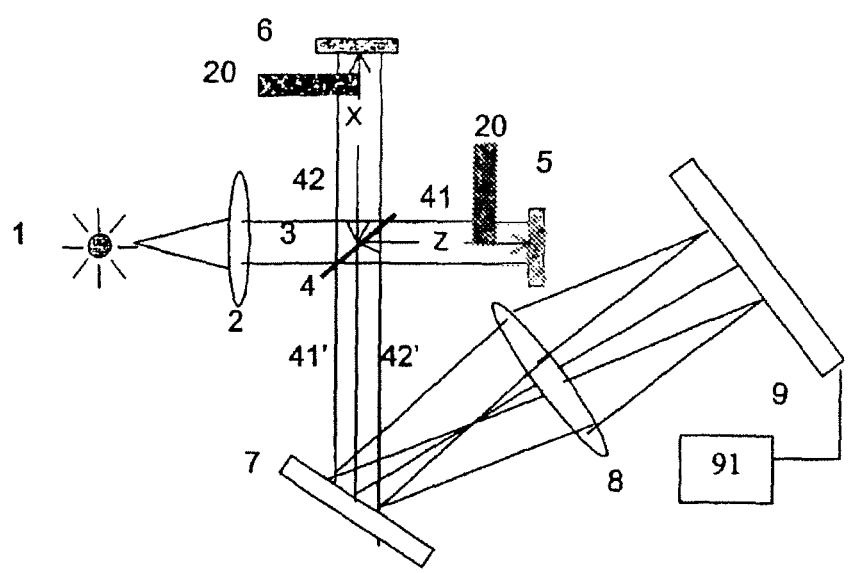
FIG. 2 shows a prior art apparatus in which the two sides of the beams inside a Michelson interferometer are split in order to generate Talbot bands.

The role of the zoom elements 31 and 32 is to give more freedom in the adjustment of the OPD range than provided by the screens 20 in the prior art apparatus of FIG. 2. Based on the explanations above, if the diameter of the relatively displaced object beam 41' is such as $N_O$ grating lines are excited, then the object wave-train is $\lambda N_O$ long after the grating. Similarly, if the diameter of the reference beam 42' is such as $N_R$ grating lines are excited, then the reference wave-train after the grating is $\lambda N_R$ long. In the case L, there is an intrinsic delay $P\lambda + \lambda N_O$ between the leading edges of the object and reference wavetrains after the grating and an intrinsic delay of $P\lambda + \lambda N_R$ between the trailing edges of the object and reference wavetrains after the grating. In the case R, there is an intrinsic delay $P\lambda + \lambda N_R$ between the leading edges of the object and reference wavetrains after the grating and an intrinsic delay of $P\lambda + \lambda N_O$ between the trailing edges of the object and reference wavetrains after the grating.

If the gap g between the two relatively displaced beams 41' and 42' is such as P grating lines are not excited, then the minimum OPD required for interference of the two wavetrains in the case L is given by:

$$OPD_{min} = P\lambda + L_C$$

and the maximum OPD when there is no overlap of the wave-trains is given by:

$$OPD_{max} = P\lambda + \lambda N_O + \lambda N_R.$$

In the case R, the sign of the $OPD_{min}$ and $OPD_{max}$ in the two equations above will change. Thus, by adjusting the gap between the two relatively displaced beams and their beam diameter, the range of measured OPD can be conveniently adjusted.

As explained in Podoleanu's papers mentioned above, the visibility of the channelled spectrum depends on the amount of overlap of the two wavetrains. Therefore, in the case L discussed above, when each relatively displaced beam covered $N\lambda/2$ grating line, the visibility increases from zero for $OPD=L_C$ to a maximum when the $OPD=N\lambda/2$, In order to enhance the strength of the signal for small OPDs, it may be desirable to partially superpose laterally the two displaced beams. This reduces the intrinsic delay between the wavetrains in the two relatively displaced beams to less than $N\lambda/2$. Consider that S grating lines are covered by both laterally displaced beams. This will have the disadvantage of allowing scattering points in the range OPD<0 to generate a non-zero visibility. More precisely, peaks will be produced in the Fourier spectrum of the signal delivered to the analyser 91 for OPD>$OPD_{min}$=−S$\lambda$.

Peaks in the range −S$\lambda$ to $L_c$ will be superposed to peaks corresponding to the range $L_c$ to S$\lambda$ leading again to an incorrect A-scan profile. However, if the region of OPDs in front of the tissue is clear up to OPD=−S$\lambda$, then no peaks will appear in the Fourier spectrum allowing for such an adjustment to be performed with the advantage of enhanced strength of the A-profile for small OPD values.

Figure 5:
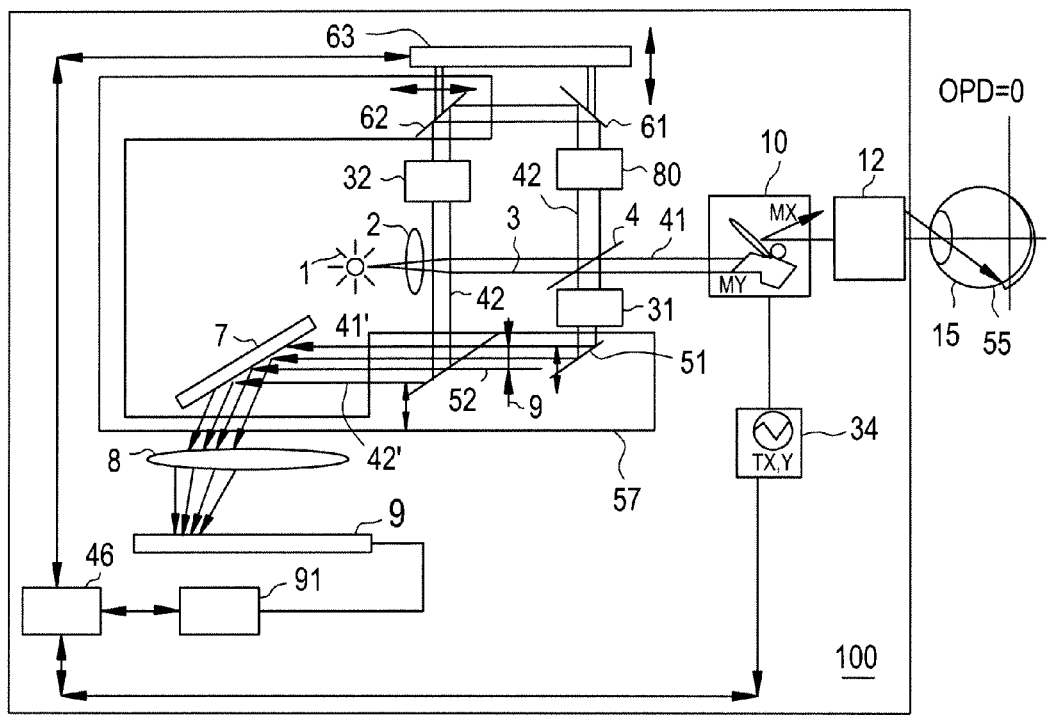
FIG. 5 shows a second embodiment of a spectral interferometry apparatus according to the invention that is selective in OPD which can deliver OCT B scan images or 3D volumetric data of a scattering or multi-layered object.

FIG. 5 is a diagram showing a second embodiment of a spectral interferometry apparatus selective in OPD according to the present invention. The embodiment shown in FIG. 5 is similar in construction to that described in relation to FIG. 3, but additionally comprises a generator 34 connected to the processor 46, an XY scanner head 10, scanning optics 12, and a focussing element 15. The apparatus is arranged to deliver not only A-scans but also 3D tomographic volumetric data from a multi-layered object 55.

Let us consider the direction of the emergent object beam 41 out of the XY scanner head 10, when not driven, as defining the optic axis. Consider a coordinate system in which X and Y are coordinate axes in a plane perpendicular to the optic axis, and Z is a coordinate axis parallel to the optic axis.

The XY scanner head 10 is provided to scan the object beam 41 over the target object 55 transversally via the scanning optics 12. A focusing element 15 focuses the light on the target object 55, for example tissue, to be examined. Without loss of generality, the retina of an eye is shown in FIG. 5 as the target area of the object 55, and the focusing element 15 is the eye lens. If the tissue 55 is skin, then the scanning optics 12 is modified in such a way that the rays after the focusing element 15 would normally evolve parallel with the depth axis. It will also be appreciated that focusing can also be performed by altering the optics inside the scanning optics 12, or by moving the collimating element 2, or by adding suitable optical elements between the beamsplitter 4 and the scanner head 10. Such elements used separately or together perform the function of focusing means applicable to multi-layer objects 55 such as retina of an eye or skin. The scanning is under the control of the generator 34. For each point (X,Y) in a transverse section, an A-scan is generated by the apparatus, using the same elements as the embodiment in FIG. 3. When one scanner is fixed, a section in the tissue in the plane (X,Z) or (Y,Z) where Z is oriented along the depth can be obtained. This is called an OCT B-scan image according to the terminology in ultrasound. When B-scans are repeated along the other coordinate axis, Y or X respectively, the whole volume of the tissue can be investigated. Alternatively, the two coordinates could be polar in the transverse plane rectangular to the optic axis. Furthermore, the scanners can be driven in such a way to generate a circular shape in a transverse section, in which case the B-scan image is along the lateral size of a cylinder oriented along the depth axis.

The processor 46 in FIG. 5 has further functionality to that described in relation to FIG. 3, in the sense that generates B-scan images from A-scan profiles and synchronises the A-scan generation of the analyser 91 with the movement of the one or both transverse scanners. More functionality is required in generating 3D volumetric data when many B-scan images are produced in synchronism with controlling both scanners in the XY-scanner.

Figure 6:
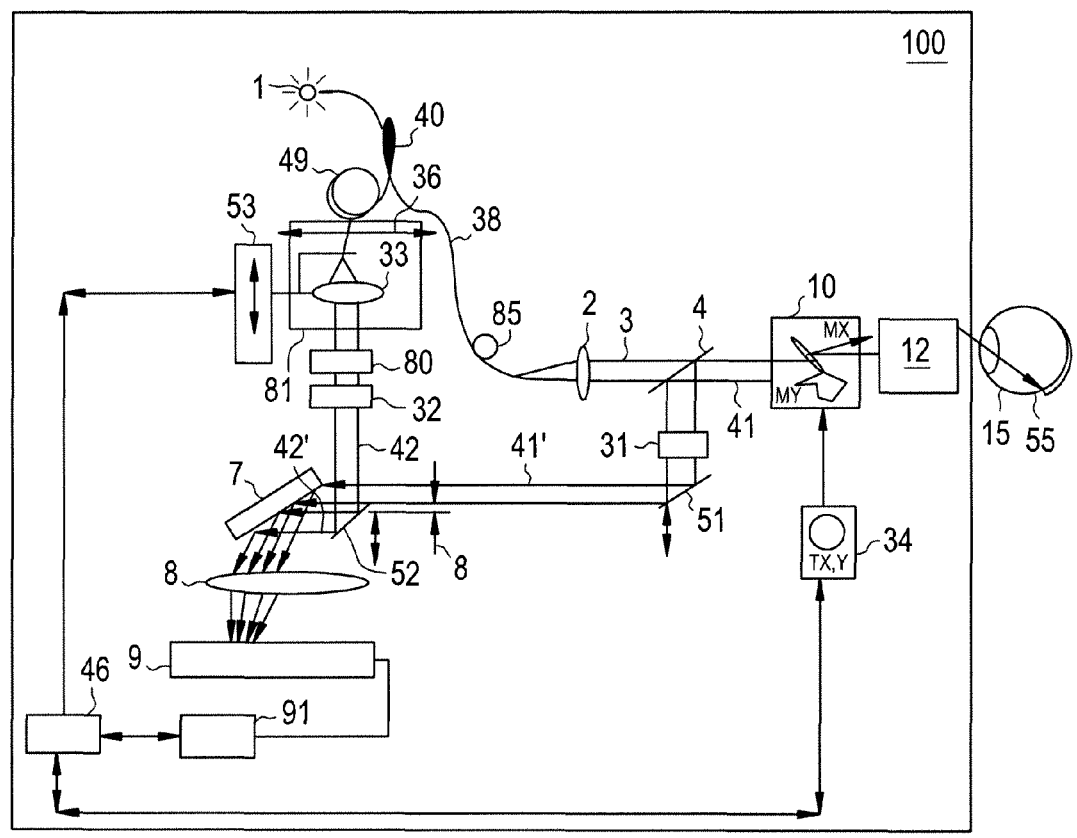
FIG. 6 shows a third embodiment of a spectral interferometry apparatus according to the invention that is selective in OPD which can deliver OCT B scan images or 3D volumetric data of a scattering or multi-layered object.

FIG. 6 shows a third embodiment of a spectral interferometry apparatus selective in OPD according to the present invention. This embodiment can be used to deliver OCT B scans and perform 3D investigation of a multi-layered object 55. In this embodiment, a hybrid configuration of optical fiber and bulk optics is employed.

The embodiment shown in FIG. 6 employs a single mode directional coupler 40 to split light from a source 1 into an object beam at the output of a fiber lead 36 and a reference beam at the output of the fiber lead 38. The fiber lead 36 is arranged to feed light into the collimating element 2. The remainder of the object path optics of FIG. 6 are similar to those discussed in relation to FIG. 5. The light collimated by the focusing element 2 forms the beam 3 that is sent via the beamsplitter 4 along a first optical path 41 towards the scanning element 10 via the scanning optics 12 and the lens 15, towards the object 55. The back-scattered light from the object 55 returns along the first optical path 41 and is deflected by the beamsplitter 4 along a third optical path that leads to a mirror 51 via a zoom element 31.

A fiber loop 49 is provided before the output of the fiber lead 38, and the fiber lead 38 is arranged to feed light into the collimator 33 to form the reference beam 42. This is sent along a second optical path 42 to a mirror 52, via a zoom element 32. In this embodiment, the fiber lead 38 is positioned on a transition stage 81, which is itself positioned on a transition stage 63. The function of the transition stage 63 is the same as described above in relation to the previous embodiments. The transition stage 81 is used to move the position of the fiber lead 38. In other embodiments, the transition stage 81 need not be present.

For polarization matching, a supplementary polarisation controller 85 is provided in the fiber lead 36 in the object optics in addition to polarisation controller 80 provided for the free space beams in the reference optics. As for the previous embodiments, the polarisation controllers are not essential, and can be removed.

As in the embodiment of FIG. 5, the mirror 51 and mirror 52 are used to displace the object and the reference beam laterally in relation to each other, to create the relatively displaced object beam 41' and relatively displaced reference beam 42', before hitting the spectral analysing element 7. As with the previously discussed embodiments, the mirrors 51 or 52 could be replaced by beamsplitters.

To adjust the position at which OPD=0, different implementations are possible as can be envisaged by those skilled in the art. One such possibility is shown in FIG. 6, where the end of the fiber lead 38 and collimator 33 in the reference path are placed on an axial scanner 63 and the fiber lead 38 is equipped with a fiber loop 49 to allow for movement.

It will also be readily apparent to those skilled in the art that the beam diameter of the relatively displaced reference beam 42' can be adjusted using collimating elements 33 of different focal length, and that the zoom element 32 can be removed. Similarly, the beam diameter of the relatively displaced object beam 41' can be adjusted using collimating element 2 of different focal length and the focus elements along the first path, in which case the zoom element 31 can be removed.

In this embodiment, the positions and tilts of the mirrors 51 and 52 are adjusted manually. However, it will also be readily apparent to those skilled in the art that the displacing means can also be put under the control of processor 46 to adjust the gap between the two beams in the displacement plane in order to adjust the minimum path difference to be sensed. For instance, this could be implemented in FIG. 5 by using another translation stage in top of the translation stage 63 to move the mirror 62 in the direction of the arrow, or both mirrors 61 and 62.

Furthermore, it will also be appreciated that the transition stage 81 can also be used to adjust the relative displacement of the beams in the arrangement shown in FIG. 6. The translation stage 81 can move the fiber end 38 and focusing element 33 in a direction perpendicular to the arrow of moving translation stage 63, and in the plane of the drawing, thus affecting the displacement of the beams and acting as displacement means.

It will be understood that in FIG. 6, the beams 42 and 41 may be in different planes to each other and may lie outside the drawing plane. In these circumstances, the reflectors 51 and 52 are used to compensate for such misalignment and to put the beams 41' and 42' in the displacing plane before hitting the dispersing element 7. The displacing plane of the two beams 41' and 42' may be out of the plane of the drawing as well. In such a case, it is essential that the dispersing element 7 is tilted, in such a way that the normal to the surface of the prism (or first prism) or diffraction grating (or first diffracting grating) in the element 7 is perpendicular to the line connecting the centres of the two displaced beams drawn in a direction perpendicular to the two beams. It will be understood that the direction of spectrally dispersed rays after the element 7 comes out of the drawing plane, and therefore the focusing element 8 and reading element 9 have to be realigned to maximise the contrast of the channelled spectrum, i.e. the normal to the centre of the focusing element 8 and to the centre of the reading element 9 are in the new plane defined by the fan of dispersed rays.

Figure 7:
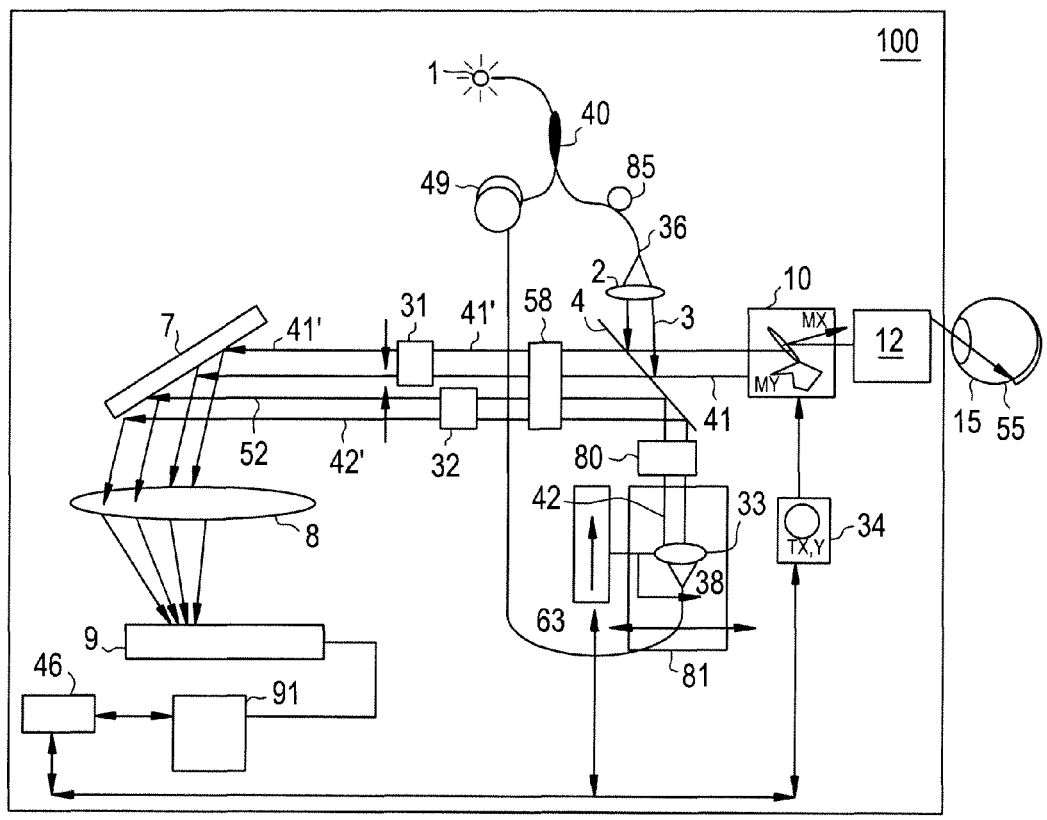
FIG. 7 shows a fourth embodiment of a spectral interferometry apparatus according to the invention.

A fourth embodiment of the invention is shown in FIG. 7. This embodiment is similar to that described in relation to FIG. 6 and illustrates another possibility for displacing the object and reference beams in order to produce relatively displaced beams.

In this embodiment, a single mode directional coupler 40 splits light from a source 1 into an object beam at the output of a fiber lead 36 in object path optics and a reference beam at the output of the fiber lead 38 in reference path optics.

The object path optics are similar to those described in relation to FIG. 6. As for the arrangement of FIG. 6, the reference path optics comprise a fiber loop 49 provided before the output of the fiber lead 38, and the fiber lead 38 is arranged to feed light into a collimator 33 to form the reference beam 42. The fiber lead 38 is positioned on a transition stage 81, which is itself positioned on a transition stage 63. The function of the transition stage 63 is the same as described above in relation to the previous embodiments.

In contrast to the arrangement of FIG. 6, the beamsplitter 4 in this embodiment is used by both object beam 41 and reference beam 42 and the gap between the two displaced beams is adjusted by moving the stage 81 which holds the fiber end 38 and collimator 33 laterally.

Therefore, in this arrangement, the beamsplitter 4 not only functions as the main splitter in the object path optics but also as a mirror for the purpose of displacing laterally the reference beam 42. Therefore, the displacing means in this embodiment includes the means to move the fiber end 38 and the beam splitter 4.

In the arrangement shown in FIG. 7, the ratio of the beam splitter 4 is such that the object beam returned from the target object 55 incurs little attenuation, which is achieved by beam splitter 4 having larger transmission than reflection coefficient. It will be appreciated that the arrangement of FIG. 6 will have a larger reflection than transmission coefficient.

In this embodiment a further mirror arrangement 58 is arranged to receive the relatively displaced reference beam 41' and the portion of the object beam that passes though the beam splitter 4 having been reflected from the target object 55. This mirror arrangement 58 is used to tilt the beams from the beam splitter 4 in order to further adjust the relative displacements. However, in other embodiments, the mirror arrangement need not be present and the displacing means could only comprise the combination of the beam splitter 4 and the transition stage 81.

Zoom elements 31 and 32 are provided in the path between the mirror arrangement 58 and the dispersing element 7. These zoom elements can alter the diameter of the relatively displaced beams in the same manner as discussed above. It will be appreciated that, as for the above described embodiments, the zoom elements 31 and 32 are optional. The zoom elements could also be placed before the displacing means.

A circulator with three input ports could be used to replace the beam splitter 4 in both the arrangements discussed with reference to FIGS. 6 and 7 in order to improve the collection of signal back-reflected from the object 55, in which case the circulator input (first port) is tied up directly to the fiber 36, the second port is directed towards the scanner head 10 and the third port can be used to send light via a collimator towards the mirror 51. Even more, two such circulators could be used, as shown in FIG. 8.

Figure 8:
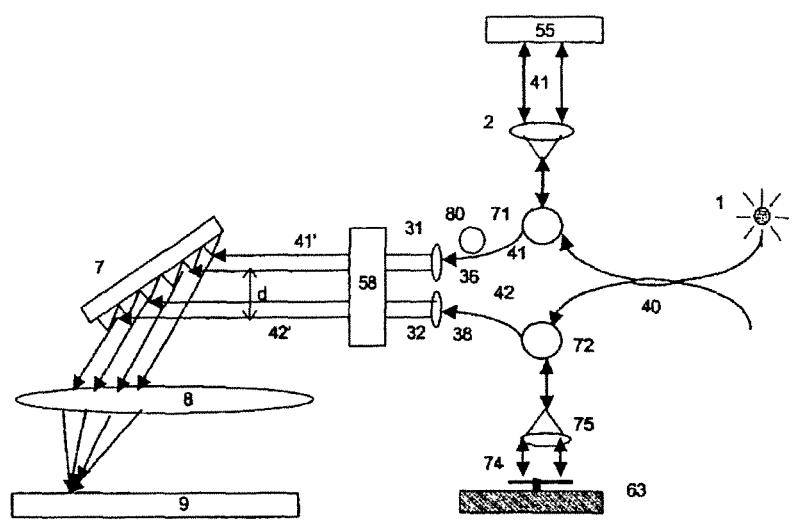
FIG. 8 shows a fourth embodiment of a spectral interferometry apparatus according to the invention.

A fifth embodiment of the invention is shown in FIG. 8. In this embodiment, both the object an reference optics use in-fiber circulators.

In this embodiment, a single mode directional coupler 40 splits light from a source 1 into an object path and a reference path. Light travels along the object path to an object circulator 71. Light output from the object circulator 71 is sent towards the target object 55 in optics via a focusing element 2 and the light returned from the target object 55 is sent back to the circulator 71 towards a fiber end 36.

Light travels along the reference path from the single mode directional coupler 40 to a reference circulator 72. Light output from the circulator 72 is sent via a focusing element 75, which in this embodiment is a lens, towards a mirror 74 on a translation stage 63. The light returned from the mirror 74 in the reference optics, is sent via the circulator 72 towards a fiber end 38.

Light from the object optics is output from the fiber end 36 passes through a zoom element 31, which in this embodiment is a gradient index lens (GRIN) lens. Light from the reference optics is output from the fiber end 38 and passes through a zoom element 32, which in this embodiment is also GRIN lens. In this embodiment, both the fiber ends and respective zoom elements are mounted on stages (not shown) which can adjust the relative positions of the fiber ends.

The light from the zoom elements 31 and 32 then passes through a mirror arrangement 58. The two beams 41' and 42' output from the mirror arrangement 58 are relatively displaced with respect to each other and fall on different portions of the dispersing element 7.

In this embodiment, the relative displacement of the beams 41' and 42' (e.g. the gap between the two beams 41' and 42') is adjusted by the combination of the mirror arrangement 58 suitably reflecting the beams, the stages (not shown) moving the relative positions of the fiber ends 36 and 38 and the GRIN lens altering the diameter of the beams (and thus the gap between them).

However, in other embodiments, the displacement of the beams falling on the dispersing means can only be adjusted by the mirror arrangement 58, with the stages for the fiber ends and the zoom elements being optional. Furthermore, the displacement can only be adjusted by the movement of the fiber ends, with the mirror arrangement 58 and zoom elements being optional. In addition, the displacement can only be adjusted by the zoom elements altering the diameters of the beams, with the stages for the fiber ends and the mirror arrangement 58 being optional.

Alternatively, the displacement could be achieved by a combination of any two of the above three factors.

It will be appreciated that the gap between the beams 41' and 42' could be made zero in the arrangement of FIG. 8 with the mirror arrangement 58 comprising a beam splitter and at least one mirror. One mirror is used to turn the beam by 45° and then turned in the opposite direction by 45° via a second mirror and launched closely to the other beam. In this case, the gap is small but it cannot be made zero nor the beams overlap. If the second mirror is a beamsplitter, then the two beams can be brought to total overlap, as shown in FIG. 5.

Other zooming elements could be mounted before or after the mirror arrangement to alter the diameter of the beams launched towards the dispersing element 7.

Furthermore, transverse scanners can be used in the object optics after the collimating element 2, or maintained in fiber leading to a multiplexed array of sensors. These could be used to scan the target object 55 in the manner described above in relation to FIGS. 5 and 6.

In this embodiment, the optical path difference in the interferometer is adjusted by movement of the transition stage 63 in this embodiment. Alternatively, the OPD in the interferometer can be adjusted using what is called as the spectral scanning delay line, as described in US patent 20030137669A1, by A. M. Rollins, "Aspects of basic OCT engine technologies for high speed optical coherence tomography and light source and other improvements in optical coherence tomography", where light is deviated angularly using a galvanometer mirror behind a diffraction grating or prism, which operates on the basis of transforming a linear phase in optical frequency in a temporal delay based on principles developed initially for processing of femtosecond laser pulses. Such a method presents the advantage of compensating for dispersion as well. Spectral scanning delay lines in transmission can also be used in the embodiments in FIG. 3, 5, 6, 7, and such a device is disclosed in the U.S. Pat. No. 6,564,089 B2, by J. A. Izatt, "Optical Imaging Device".

A sixth embodiment of the invention will be described in relation to FIG. 9. In this arrangement, a relatively displaced object beam 41' and a relatively displaced reference beam 42' are provided to a beam splitter 99. The relatively displaced beams could be produced in any of the ways discussed above, e.g. by reflection, deflection, refraction, alteration of the beam diameters, movement of fiber ends or any combination of these.

The beam splitter 99 therefore produces two sets of relatively displaced beams. One set of relatively displaced beams 41' and 42 are provided to a mirror arrangement 59 which can further adjust the relative displacement of the beams. As shown in FIG. 9, the mirror arrangement 59 can adjust the lateral gap between the beams from a value of g prior to the beam splitter to g' after the mirror arrangement 59. The relatively displaced beams 41' and 42' are then output to dispersing means 7, which disperse their spectral content onto reading element 9 in the manner discussed above. The reading element 9 provides an electrical output to a spectrum analyser 91.

The other set of relatively displaced beams 41 are provided to a second mirror arrangement 59' which can also further adjust the relative displacement of the beams. As shown in FIG. 9, the mirror arrangement 59' can adjust the lateral gap g between the beams from prior to the beams from a value of g prior to the beam splitter to g" after the mirror arrangement 59'. The beams output from the mirror arrangement 59' can be considered second relatively displaced beams 41" and 42". The second relatively displaced beams 41' and 42' are then output to second dispersing means 7', which disperse their spectral content onto a second reading element 9' in the manner discussed above. The second reading element 9' provides an electrical output to a second spectrum analyser 91'.

As in the previously described embodiments, the dispersed light is focused by elements 8 and 8' on the reading elements 9 and 9'. From the above, it will be appreciated that the gap between the two beams (i.e. g' or g") generates an intrinsic delay in the combination of dispersing means, focussing element 8 and reading element 9 and a second intrinsic delay in the combination of the second dispersing means, second focussing element 8 and second reading element 9. The orientation and spatial position of the two dispersing means 7 and 7' in relation to the direction of the respective incoming displaced beams is such that the intrinsic delay and the second intrinsic delay are of opposite sign.

In this embodiment, diffraction gratings are used as both the dispersing means 7 and the second dispersing means 7, and the intrinsic delay and the second intrinsic delay being of opposite sign is achieved by the diffraction grating in the dispersing means 7 being arranged to diffract orders of opposite sign to the diffraction grating in the second dispersing means 7.

If the dispersing means 7 and the second optical dispersing means 7 each comprises one or more prisms, the one or more prisms can arranged such that one of the relatively displaced object beam 41' or the relatively displaced reference beam 42' is closest to prism apex in the dispersing means 7 and the second relatively displaced reference beam 42" or the second relatively displaced object beam 41' respectively is closest to the prism apex in the second optical dispersing means.

As a consequence of the above, it will be appreciated that one spectral analyser 91 outputs signal for one sign of the OPD, for example for the positive OPD values ("channel P"), while the other spectral analyser outputs signal for the opposite OPD sign, i.e. negative OPD values ("channel N").

The gaps g' and g" between the two relatively displaced beams in each channel can be adjusted separately by mirror arrangements 59 and 59'. In this embodiment, the mirror arrangements 59 and 59' comprise mirrors and stages similar to those described above in relation to FIGS. 3, 5, 6, 7, 8 in order to displace the two beams laterally. However, it will be appreciated that any of the other elements that can form the displacing means discussed above could replace the mirror arrangements 59 and 59'. Furthermore, it will be appreciated that only one such additional displacing means can suffice.

These use mirrors and stages similar to the procedures used in FIG. 3, 5, 6, 7, 8 to displace laterally the two beams. In principle, the two beams can even be superimposed by using the displacing element, even if the initial gap, g, was different from zero. The use of two displacement means allow separates adjustment in the two channels of the absolute value of the minimum OPD which can be sensed and of the position in depth where maximum sensitivity is achieved in each channel.

If utilised in combination with any of the embodiments discussed above, the electrical spectrum analyser 91 could be used to provide an A-scan for positive (or negative) sign OPD and the second electrical spectrum analyser 91' could provide an A-scan for negative (or positive) sign OPD.

In this embodiment, a synthesising element 92 is provided to receive the output of the spectrum analyser and the second spectrum analyser 91'. The synthesising element 92 joins the two A-scans to provide an A-scan for double the range of depths given by the individual spectrum analysers 91 and 91'.

In order to make sure that each channel has visibility nonzero for one sign of the OPD only such a dual channel embodiment requires that there is no overlap of the two sets of relatively displaced beams. In this way, there is no cross-talk between the two channels, P and N, i.e. for a given OPD of any sign, a signal appears at the output of either spectrum analyser 91 or 91' and never in both.

If each channel has a range $|OPD|_{max}=D$, then the synthesising element 92 will provide signal in the range −D to D, i.e. double the range of each channel, but with a gap in the centre, of $-L_c$ to $L_c$ about OPD=0. If the gap is larger than the beam diameter, then the minimum |OPD| in each channel exceeds the coherence length and the gap about zero path imbalance widens.

Figure 9:
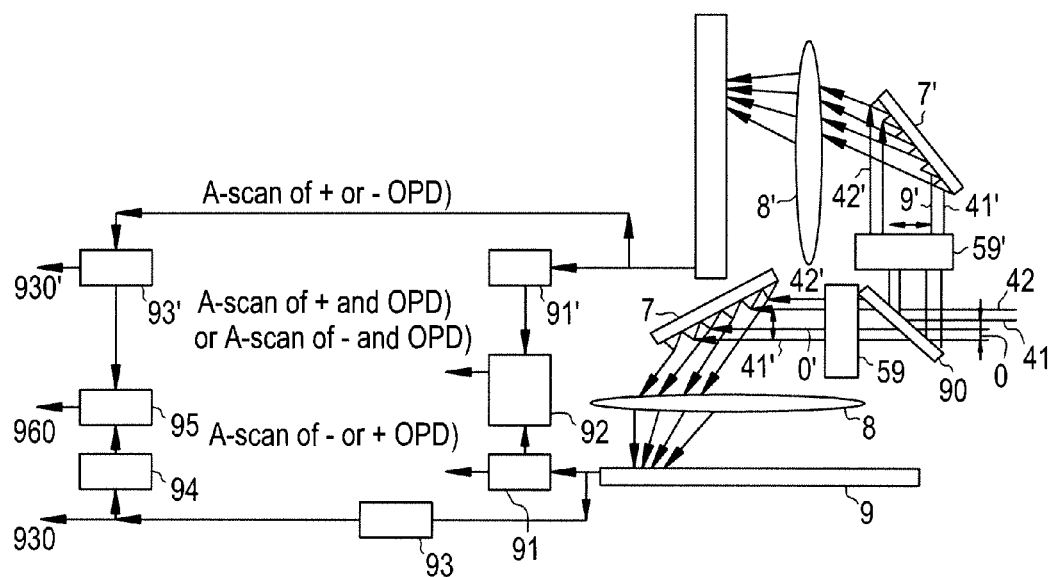
FIG. 9 shows a modification applicable to all previous embodiments of the spectral interferometry apparatus according to the invention in order to provide signal irrespective of the OPD sign.

If the arrangement in FIG. 9 is used to build a B-scan OCT image out of several A-scans in the range −D to D, then the image will have vanishing contrast (low contrast, tending to zero) in the middle of the image, about zero path imbalance. Whilst this may be considered disadvantageous for imaging purposes, it has the advantage that at no moment the image will be distorted by mirror terms irrespective of the object movement. Each pixel in the image will correspond to a given sign of OPD only, with no cross-talk due to the OPD of the same modulus but opposite sign.

The A-scan output characteristic of the embodiment in FIG. 9 will be discussed in relation to FIGS. 10*a* to *c*.

Figure 10A:
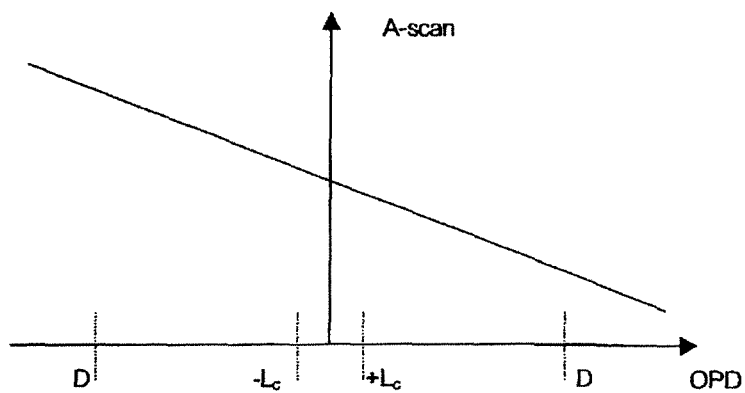
FIG. 10a, FIG. 10b and FIG. 10c. show the A-scan output of the embodiment in FIG. 9.
Figure 10B:
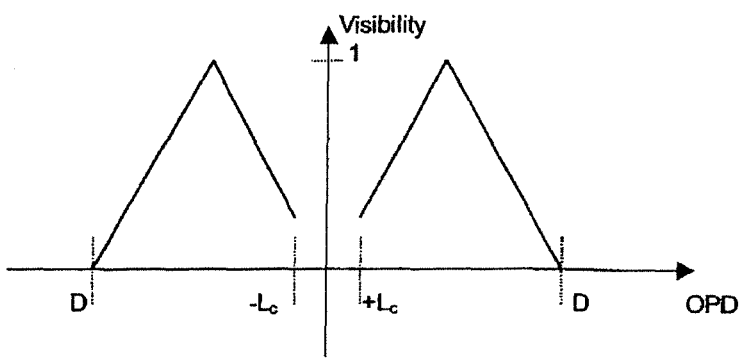

FIG. 10*a* shows a hypothetical decay of the reflectivity in depth which for simplicity is considered as being linear with depth. FIG. 10*b* shows the two visibility profiles of the two channels of the arrangement of FIG. 9, one channel in the regime L of operation selecting the positive OPDs and the other channel in regime R selecting the negative OPDs, with the results summed up in the synthesising element 92.

Figure 10C:
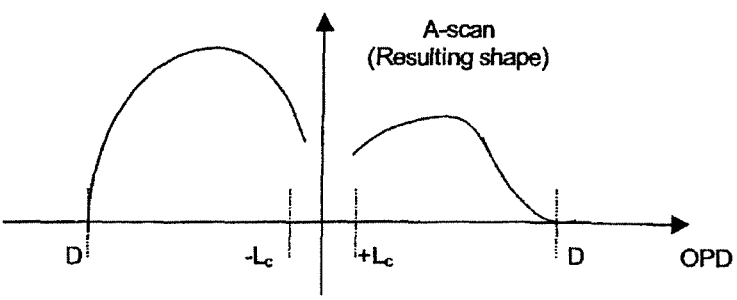

The combined effect of the overall visibility profile of the embodiment in FIG. 9 with the decay shown in FIG. 10*a* leads to a final decay in the range of negative and positive OPDs, as shown in FIG. 10*c*.

For comparison, the output of a known method that uses phase shifting interferometry for removing the mirror terms will be discussed in relation to FIG. 11*a* to *c*.

Figure 11A:
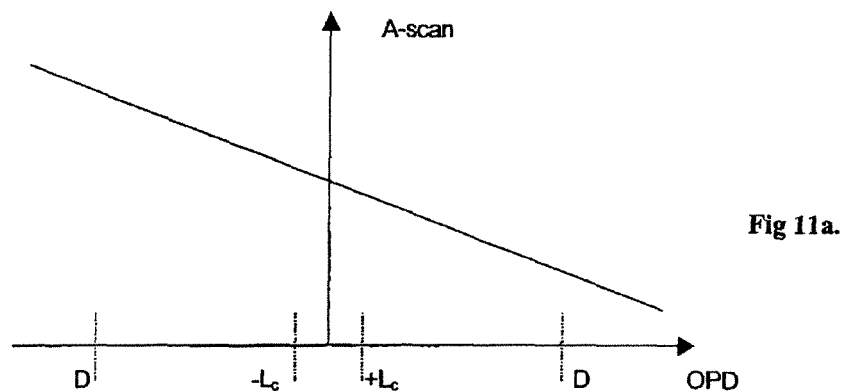
FIG. 11a, FIG. 11b and FIG. 11c. show the output signal of a prior art apparatus equipped with phase shifting interferometery to deliver unambiguous A-scans free of the mirror terms.

FIG. 11*a* shows a hypothetical decay of the reflectivity in depth which for simplicity is considered as being linear with depth, the same as that shown in FIG. 10*a*.

Figure 11B:
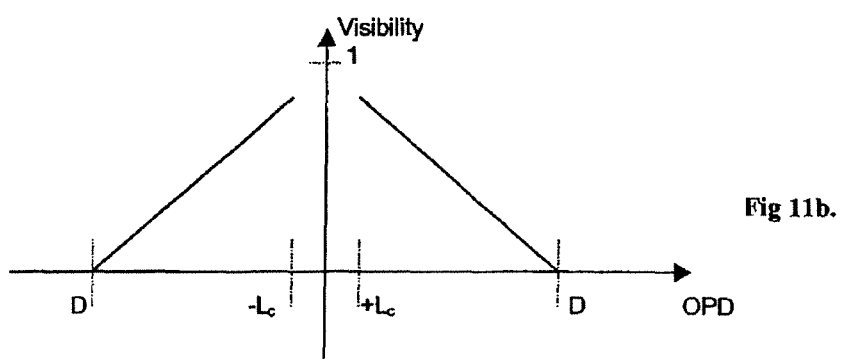

The visibility profile for the known method of avoiding the mirror terms by using phase shifting methods is shown in FIG. 11*b*, with maximum about OPD=0.

Figure 11C:
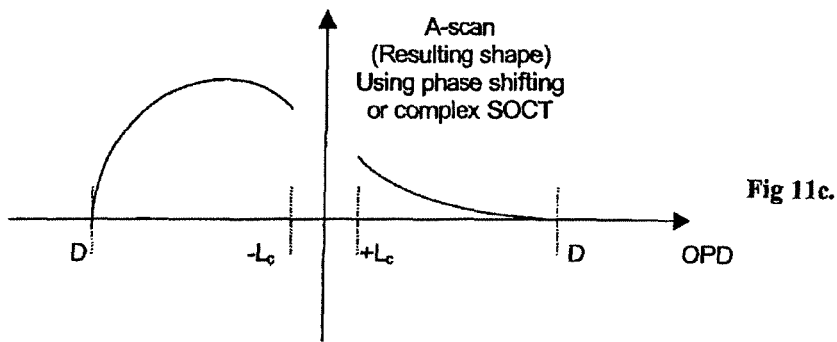
Figure 12:
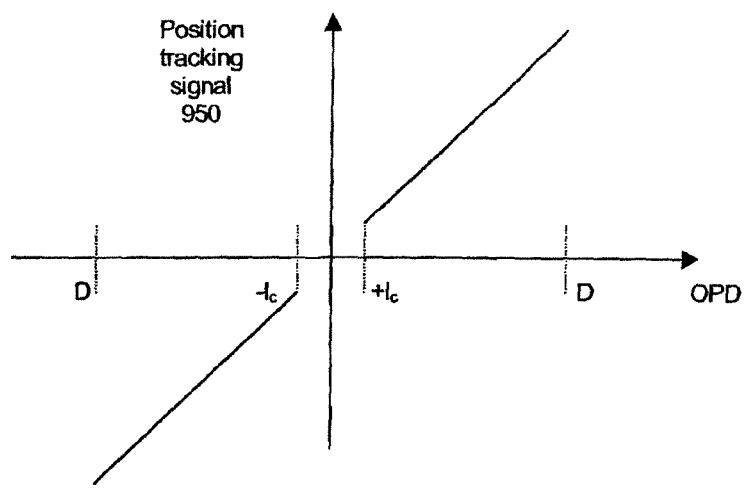
FIG. 12 shows the position tracking signal of the axial position of a single layer object that can be delivered by embodiments of the invention.

The combination of the decay shown in FIG. 11*a* with the overall visibility profile in FIG. 11*b* leads to the resulting profile shown at FIG. 11*c*.

Both methods, that according to the present invention as well as that used in the art for avoiding mirror terms based on phase shifting interferometer and at least 3 measurements lead to a distorted A-scan profile. Both methods output no Fourier Transform signal, as no channelled spectrum exists for |OPD| less that the coherence length, however our methods delivers vanishing values for |OPD| just above the coherence length, while the phase shifting method delivers the maximum strength signal. The method according to the present invention enhances the contrast of the image at two depths in the object while the known method in the art around the OPD=0. It will be appreciated that, in both cases, the correct A-scan profile can be in principle inferred by deconvolving the output results shown in FIG. 10*c* and FIG. 11*c* with the visibility profiles in FIG. 10*b* or FIG. 11*b* respectively. However, the method and apparatus according to the invention are tolerant to the object movement while the state of the art method requires at least 3 measurements to produce the results in FIG. 11*c*.

The approximated profiles of the A-scans shown in FIG. 10*c* and FIG. 11*c* consider a large depth of focus. In practice however, the confocal profile of the focusing optics may be narrower than the depth range D, in which case to infer the correct profile of the A-scan, the visibility has to be multiplied with the confocal profile due to focusing. The difference in the visibility profile between that shown in FIG. 10*b* and the state of the art shown in FIG. 11*b*, requires a different adjustment of the focus position in the target object, for example tissue. In the state of the art case, to compensate for the decay in the visibility versus OPD, the focus is adjusted all the time deep in the tissue, while in the present disclosure, the focus may be adjusted either close to OPD=0 or close to OPD=D=Nλ in order to flatten the overall sensitivity of the apparatus.

In addition, such embodiments of the present invention offer an unique possibility of selection in the OPD value, where the focus may be adjusted to coincide with the visibility maximum position, close to Nλ/2, in which case a narrow profile results around Nλ/2, not possible with the state of the art case, where the visibility continuously decreases with OPD, from the maximum achieved at the OPD=$L_c$, as shown in FIG. 11*b*.

The embodiment discussed in relation to FIG. 9 can be generalised to reading S sensors or generating OCT images from a target object 55 where different S channels select their own OPD range, with a distinct minimum OPD and a distinct OPD value where the sensitivity achieves a maximum. To achieve this, the beamsplitter 99 could be replaced by several optical splitters in order to provide pairs of object and reference beams to S number of optical dispersing means, 7, 7', 7", 7''' . . . each equipped with their own reading elements 9, 9', 9", 9''', . . . and their own displacing means 57, 57', 57", 57''', . . . Only two channels were shown in FIG. 9, each sensitive to a sign of OPD, therefore named P and N. When several S channels are used, some could be made sensitive to positive OPD, channels P and some to the negative OPD, channels N.

Furthermore, although the arrangement shown in FIG. 9 provides two relatively displaced beams (with a gap g) to the beam splitter 99, other embodiments could provide the beam splitter 99 with object and reference beams with no displacement. Such embodiments would then use a displacing means in each channel to adjust the displacement of the beams in each channel.

If the object is a single layer surface, then embodiments with different channels such as those described in relation to FIG. 9 can be used to accomplish a different function than imaging.

FIG. 9 shows two frequency to amplitude converters 93 and 93', which receive outputs from the reading elements 9 and 9'. The frequency to amplitude converters 93 and 93' perform conversion of the frequency of the signal delivered by the reading elements 9 and 9' respectively into magnitude, irrespective of the signal input amplitude, i.e. the larger the |OPD|, the higher the strength of the output signal. However, if one of the signal out of the frequency to amplitude converters is inverted by an inverter 94 and the result summed with that of the other converter in the adder block 95, then a DC signal, 950 is obtained that is proportional to the OPD, covering positive and negative values for the positive and negative values of the OPD in the range of −D to +D.

Similarly, partial use may have the output signals 930 or 930', each for one sign of the OPD only, in tracking the axial position of a mirror. It will be apparent that the same is true for embodiments such as those presented in FIG. 3, 5, 6, 7, 8, which can be tuned to be sensitive to one sign of OPD only. Such embodiments, like that in FIG. 9 or embodiments in FIG. 3, 5-8 equipped with one frequency to amplitude converter, may have immediate application in the fast tracking of the axial position of the cornea of a living eye.

Because the method according to the invention is sensitive to the OPD sign, a novel method can be devised to measure the thickness of a plate, such as a microscope slide. Let us consider that the optical plate thickness is less than D/2, where D is the OPD range of each of the channels in an arrangement such as that shown in FIG. 9. If the plate position randomly oscillates along the depth axis, then it is possible that:

(a) Both interfaces are in the positive OPD range;
(b) One interface is in the positive OPD range and the other in the negative OPD range;
(c) Both interfaces are in the negative OPD range.

For cases a and c, when both interfaces are in the same OPD range, two peaks are present in the A-scan of each channel while the A-scan of the other channel does not present any peaks. In this case, the thickness can be inferred by deducting the two OPD values corresponding to the positions of the two peaks in the A-scans.

For case b, the A-scans of the two channels, each presents one peak only. In this case, the thickness could be inferred by adding the frequencies of the two peaks, with one frequency delivered by each channel only. Alternatively, a summation of the signals 930 and 930' could provide the thickness.

Irrespective of the case above, a, b, c or the processing method used, A-scans delivered by the electrical signal analysers 91, 91' or the synthesiser 92, or by the frequency converters, 93 and 93', the thickness value obtained is tolerant to the axial movement of the microscope slide.

This method could be extended to the rapid measurement of the retina thickness for topography or cornea thickness, tolerant to the axial eye movement. To avoid false results due to the noise, thresh-holding circuits can be used after each electrical analyser 91 and 91'.

While FIG. 9 is shown as having amplitude converters 93 and 93' and signal analyser 95, these are not essential if only imaging is required.

The embodiments described above in relation to FIGS. 3, 5, 6, 7 and 8, having a gap between the two beams larger than the sum of the radiuses of the two displaced beams, produce an unique selection in depth. A given OPD value is translated into a frequency value, f, i.e. into a repetition of peaks and troughs in the channelled spectrum if it has the accepted sign (i.e. positive or negative depending on the arrangement). At the same time, the same OPD of opposite sign does not imprint any channelled spectrum. So, for the two cases, a frequency for no frequency is generated in the signal output of the reading element 9 and the apparatus is so sensitive to one sign of OPD only. The apparatus could become sensitive to the other sign of OPD and still recover uniquely the distribution of scatterers in depth in an object, or the distribution of OPDs in a distributed sensor by modifying the optical source, as discussed below.

If a low coherence source beam is sent via a differential delay, A, to the interferometer, then for OPD=0, a component corresponding to the differential delay is present in the channelled spectrum of frequency $f_A$. In this case, the frequency of the signal delivered by the reading element 9 for the given OPD value is again f, but another peak appears in the channelled spectrum, of frequency $f+f_A$. If the OPD in the interferometer has opposite value, then the modulation frequency is $f_A-f$. This leads to a different selection of the OPDs according to their sign, where instead of having a frequency value or not, two frequencies different from zero are generated depending on the OPD sign.

To illustrate the principle, consider that the object has an optical thickness T<D, where D is the maximum depth range in the apparatus. Consider that the spectrum dispersing means is a diffraction grating. In this case, the maximum depth range can be approximated as $D=(N_O+N_R)\lambda$, where $N_O$ and $N_R$ are the number of grating lines covered by the relatively displaced object beam and the relatively displaced reference beam respectively. Consider that the gap between the displaced beams is larger than the sum of their radiuses which makes the apparatus sensitive to one sign of OPD only. Consider that the orientation of the grating is such that the apparatus selects the positive sign of the OPD only. When all layers in the object are in the positive range of the depth, then all frequencies in the spectrum of the signal output of the reading element are in the range up to kD, where k is the apparatus conversion coefficient between OPD values and electrical frequency.

All layers are present in the A-scan delivered by the embodiment in FIG. 3 or in the B-scan images delivered by embodiments in FIG. 5-8. If accidentally the object moves closer to the apparatus, frequencies are generated for layers in the positive OPD range and no frequencies are generated for layers of the object in the negative range. Consider the extreme case where the object is so close to the apparatus that its middle thickness corresponds to OPD=0. In this case layers from T/2 up to T are displayed in the A-scans or B-scan images and layers between 0 and T/2 eliminated. However, these layers could be recovered if the low coherence beam coming from the source is duplicated and delayed by a differential delay, A, where T<Δ<D. In this case, the scatterers around the top of the object produce a frequency close to kΔ while the scatterers around the middle of the object a frequency k(Δ-T/2). The layers from T/2 to T determine frequencies in increasing order up to kT/2 while the layers in the negative OPD range are sent in inverse order in the range of frequencies k(Δ-T/2) to kΔ. The two parts of the A-scans or B-scans can be synthesised together to reconstruct the image by software means and give a correct image. If all layers go into the negative OPD range, then a continuous complete A-scan or a continuous complete B-scan is obtained for the thickness T, but oriented the other way around, from high to small frequencies, i.e. from k(Δ-T) to kΔ, however correct, with no superposition of layers (no mirror terms).

There are different ways to create a replica of a source delayed by Δ. For example, two single mode couplers in series could be used, with the two outputs of the first coupler connected to the two inputs of the second coupler to form a Mach Zehnder configuration. In this arrangement, the differential delay between the two leads of the connecting fibres between the two couplers introduce the delay. At the output of the second coupler, two replicas of the optical sources result, one for each path connecting the two couplers in between.

Alternatively, introducing a glass plate halfway through the beam 3 from the source in FIG. 3, 5, can accomplish the same task. The plate has to be introduced into the beam in the configuration A, B according to the terminology in Podoleanu's papers. This means that the left and right parts of the launching beam 3 are identical, which requires that the plate is introduced with its edge parallel with the set-up plane. When using a diffraction grating as the dispersing element, the edge of the plate is perpendicular to the diffraction grating lines.

As another alternative, a cavity low coherent source could be used. A cavity low coherent source is a laser, e.g. a laser diode, driven below threshold. In this case, the multiple reflections on the cavity laser walls has the same effect with the introduction of the delayed replica above using couplers or plates. The roundtrip within the cavity leads to the generation of repetitive replicas delayed by multiples of the cavity length. Multiple peaks appear in the electrical signal delivered by the electrical analyser 91 corresponding to OPD values equal to multiple values of the cavity length, as shown by the experiments described in Podoleanu's papers, using commercial laser diodes, at multiples of 2.2 mm.

This principle could also be used for instance in efficiently using the reminiscent ripple in the spectrum of superluminiscent diodes (SLD) as well. SLDs are non-cavity sources. In SLDs, one of the waveguide facet is angled and anti-reflection (AR) coated to avoid formation of a cavity and gain is obtained for rays traversing the active medium once only. However, tilting the waveguide and AR coating it does not eliminate the roundtrip of some rays within the active medium and SLDs exhibit satellite peaks in their autocorrelation function at OPD values 2-5 mm. These satellite peaks practically limit the maximum range of OCT depth up to their OPD values. It is advantageous in this case to introduce a differential delay using two couplers or a microscope slide plate which creates a differential delay Δ matching the satellite peak OPD.

The introduction of the differential delay between the source and the apparatus or the utilisation of a multimode laser below threshold has the effect of shifting the depth of range of interest. This could be applied in circumstances when the frequency in the output of the electrical signal analyser is close to zero for a given OPD of interest. Instead of using a frequency component f, the frequency $f+f_A$, is used. This is possible when using a differential delay smaller than half of the maximum depth range, D. This is restricted to thin objects with T<D/2, however the method is advantageous as it produces two A-scans or two B-scan images, where the visibility of scatterers varies in opposite directions within them. For the first tomogram (A or B-scan) in the range 0 to T, the visibility goes up in the first image, corresponding to frequencies up to $f_A/2$ and down in the second image of frequencies $f_A/2$ up to $f_A$.

Such methods using a source with a delayed replica could also be used in embodiments having more than one channel, such as those described above in relation to FIG. 9. The embodiment described above in relation to FIG. 9, having a gap between the two beams larger than the sum of the radiuses of the two displaced beams, produces an unique selection in depth. A given OPD value is translated into a frequency value, f, i.e. into a repetition of peaks and troughs in the channelled spectrum, and depending on the OPD sign, will be delivered by the P or the N channel. So the two frequencies generated are f but they appear at different outputs depending on the OPD sign.

If the low coherence source beam is sent via a differential delay, Δ, into the interferometer, then for OPD=0, a component corresponding to the differential delay is present in the channelled spectrum of frequency $f_A$, in both channels, P and N. In this case, the frequency for the OPD is again f, in the channel P, but another peak is noticed in the channelled spectrum of the channel P, of frequency $f+f_A$, and $f_\alpha-f$ in the other channel, N. If the OPD in the interferometer has opposite value, then the modulation frequency is f in the channel N and $f_A-f$ in the channel P. This leads to a different selection of the OPDs according to their sign, where different frequencies are generated at two different outputs.

Other embodiments and alternative arrangements to the spectral interferometry apparatus which has been described above may occur to those skilled in the art, without departing from the spirit and scope of the appended claims. For example, in the embodiments described with reference to FIG. 5, 6, 7, 8, 9, the photodetector array could be a two dimensional (2D) CCD camera. In such a situation, each row (column) could be utilized for the spectrum evaluation of the signal backscattered from pixels along a transverse line in the target object 55, and the 2D transverse scanner can be replaced by a one dimensional (1D) scanner, to scan in a direction perpendicular to that acquired by the CCD array. In this way, three dimensional (3D) volumetric data can be acquired, with one transverse direction covered by the CCD array and the other rectangular transverse direction covered by the transverse scanner.

Alternatively, the scanner in the object path can be eliminated in which case, when using a 2D CCD array, OCT B-scan images could be generated using the 2D CCD array only.

When using a 2D CCD array in the examples above, the beam 3 is collimated using the element 2 along a line normal to the plane of the drawings, of length equal to the height of the CCD array and the elements 4, 61, 62, 51 and 52 are sufficiently wide. The scanner head 10 is eliminated for B-scan imaging and if volumetric data is required a 1D scanner head is used, with sufficient size to handle and project a line over the tissue, employing means known to those skilled in the art. Analogously, if the embodiment in FIG. 5, 6, 7, 8 is used, then the elements 2 and 33 prepare linear collimated beams along lines perpendicular to the plane of the figure. Again, the scanner head 10 is eliminated for B-scan imaging and if volumetric data is required, a 1D scanner head is used, with sufficient size to handle and project a line over the tissue, employing means known for those skilled in the art.

The method and apparatuses subject to the invention are obviously compatible with methods of spectra averages or spectra evaluations collected at different accurately controlled OPD positions, methods known in the art of phase shifting spectral interferometry. By manipulating such spectra acquired at small OPD steps as subdivisions of a wavelength, further reduction of the noise can be achieved according to methods known for those skilled in the art, as mentioned above. A noisy channeled spectrum arises due to beating between the rays in the reference beam. This can be attenuated by superposing two spectra collected at a phase difference of π, as described in the paper "In vivo human retinal imaging by Fourier domain optical coherence tomography", published by M. Wojtkowski, R. Leitgeb, A. Kowalczyk, T. Bajraszewski, A. F. Fercher, in the J. Biomed. Optics 7(3), (2002), p. 457-463. Alternatively this can be attenuated by superposing several spectra at several OPD steps as described in the paper by M. Wojtkowski in Optica Applicata mentioned above. By superposing such spectra, the noise is cancelled and the channelled spectrum due to the OPD between the two beams in the interferometer is enhanced. Such a method could equally be applied to embodiments of the present invention by displacing the translation stage 63 under the control of the processor 46 in synchronism with the reading element 9, analyser 91 and the scanner 10, for each pixel in transversal section, a coordinate X in the case of B-scan image, or (X,Y) when volumetric data, is acquired. Also a number M of channelled spectra are acquired for M steps of the translation stage. After an A scan is evaluated out of the M spectra, a function which could be performed by the same processor 46, the transverse scanner is advanced to the next transverse pixel.

The method and apparatuses subject to the invention are compatible with polarization modulators. Combining elected polarization states in the two arms of the interferometer (i.e. the object and reference optics), information on the depth resolved polarization of the target can be inferred, such as Stokes vectors, as presented in "Determination of depth-resolved Stokes parameters of light backscattered from turbid media by use of polarization-sensitive optical coherence tomography", published in *Opt. Lett.*, 24, No. 5, pp. 300-302, 1999, by J. F. de Boer, T. E. Milner, J. S. Nelson, or complete Mueller matrix information as described in "Optical-fiber based Mueller optical coherence tomography", published in *Opt. Lett.*, 28, No. 14, pp. 1206-1208, 2003, by S. Jiao, W. Yu, G. Stoica, L. Wang. When these functions are implemented using the method and apparatuses according to the present invention, unique recovery of polarization sensitive A-scans is obtained and unique polarization sensitive B-scan maps are generated.

For phase resolved OCT, stroboscopic illumination together with phase modulation in one of the interferometer arms has been presented, known as the method of four buckets, as presented in {A. Dubois, L. Vabre, A. C. Boccara, et al., "High-resolution full-field optical coherence tomography with a Linnik microscope," *Appl. Optics* 41 (4), 805-812 (2002) and H. Saint-James, M. Lebec, E. Beaurepaire, A. Dubois, A. C. Boccara, "Full field optical coherence microscopy," in *Handbook of optical coherence tomography*, B. E. Bouma, G. J. Tearney eds., (Marcel Dekker Inc, New York-Basel, 2002) 299-333. The method and apparatuses according to the present invention are compatible with phase modulation and synchronous switching of the illuminating light. In this way, by combining the four spectra acquired for different phase shifts, amplitude and phase information A-scan are retrieved. The method is applicable in the detection of small deviations and Doppler OCT.

The polarization modulators or/and phase modulators, in bulk or in-fiber could be introduced anywhere in the object optics or reference optics or between the displacing means and the dispersing elements.

Throughout the disclosure, the term reflectivity was used because the majority of applications in OCT is in imaging the tissue in reflection. However, in the microscopy of biologic tissue, imaging in transmission is also used. It should be obvious for those skilled in the art to understand that the embodiments of the present disclosure as described in FIG. 5-9 can be easily altered to investigate and image the object in transmission, in which case the light is not returned to the main optical splitter 4 and the third optical path is that collecting the light from the object. Similarly, a chain of sensors can be investigated in transmission. Therefore, where reflectivity is used, this should be also understood as sampled transmission in depth when the object is investigated in transmission.

The foregoing description has been presented for the sake of illustration and description only. As such, it is not intended to be exhaustive or to limit the invention to the precise form disclosed. For example, modifications and variations are possible in light of the above teaching which are considered to be within the scope of the present invention. Thus, it is to be understood that the claims appended hereto are intended to cover all such modifications and variations which fall within the true scope of the invention.

Other modifications and alterations may be used in the design and manufacture of the apparatus of the present invention without departing from the spirit and scope of the accompanying claims.

For the scope of the invention, the multi-layer object could be tissue, but equally could signify an optical path leading to multiple optical path of different lengths to multiple sensors in a structure of multiplexed sensors, and the method disclosed here could be employed to selectively access a sensor or a group of sensors according to their OPD, either in reflection or transmission.

What is claimed is:

1. Spectral interferometry apparatus, comprising
object optics arranged to transfer a beam from the optical source to a target object, and to produce an object beam from the target object;
reference optics arranged to produce a reference beam, wherein the object beam is associated with an object path delay and the reference beam is associated with a reference path delay, the difference between the object path delay and the reference path delay defining an optical path difference, OPD;
displacement optics arranged to displace at least one of said object beam and said reference beam in order to relatively displace at least one of the object beam and the reference beam laterally from each other by a lateral displacement, G, to produce a relatively displaced object beam and a relatively displaced reference beam, wherein the displacement optics is arranged to use one or a combination of reflection, deflection, or refraction of at least one of the object beam and the reference beam; and
optical spectrum dispersing optics arranged to disperse the relatively displaced reference beam and relatively displaced object beam into a dispersed relatively displaced reference beam and into a dispersed relatively displaced object beam respectively,
wherein the dispersed relatively displaced reference beam and the dispersed relatively displaced object beam are superposed on the reading element;
wherein the dispersed laterally displaced object beam has a wavetrain length, $W_O$ and the dispersed laterally displaced reference beam has a wavetrain length $W_R$; and
wherein in use the combination of the displacement optics and the optical spectrum dispersing optics is arranged to create an intrinsic optical delay, IOD, between the two wavetrains of lengths $W_O$ and $W_R$ which can be used with the optical path difference, OPD, to generate a channelled spectrum for the optical path difference, OPD, on the reading element.

2. Spectral interferometry apparatus according to claim 1, wherein the positions of the footprints of the two relatively displaced object beam and the relatively displaced reference beam on the optical spectrum dispersing optics are adjusted from total superposition, to partial superposition or no superposition, depending on the lateral displacement, G, of the two relatively displaced beams caused by the displacement optics.

3. Spectral interferometry apparatus according to claim 1, wherein in use the combination of the displacement optics and the optical spectrum dispersing optics is arranged such that the said intrinsic optical delay, IOD, between the wavetrains $W_O$ and $W_R$ is proportional to the lateral displacement, G, of the two relatively displaced beams caused by the displacement optics.

4. Spectral interferometry apparatus according to claim 1, wherein in use the combination of the displacement optics and the optical spectrum dispersing optics is arranged such that the overall delay, OD, between the wavetrains $W_O$ and $W_R$ before reaching the reading element is a combination of the delays OPD and the IOD;

wherein the modulation intensity of the said channelled spectrum is proportional to the overlap of the wavetrain length, $W_O$ and the wavetrain length $W_R$; and wherein the maximum overlap corresponds to OD=0, when OPD=$d_m$=-IOD.

5. Spectral interferometry apparatus according to claim 4, wherein by adjusting the lateral displacement, G, of the two relatively displaced beams, the maximum of modulation of channelled spectrum versus OPD is moved from OPD=0 to deeper OPD values in the object.

6. Spectral interferometry apparatus according to claim 5, wherein $d_m$ and $d_f$ are sufficiently similar to each other to produce a narrow profile for the modulation intensity of the channelled spectrum versus OPD.

7. Spectral interferometry apparatus according to claim 5, wherein $d_m$ and $d_f$ are adjusted to be dissimilar to flatten the profile of the modulation intensity of the channelled spectrum versus OPD.

8. Spectral interferometry apparatus according to claim 5, wherein the wavetrain lengths $W_O$ and $W_R$ are proportional to the diameter of the relatively displaced object beam and to the diameter of the relatively displaced reference beam respectively, diameters that can be adjusted using focusing elements in the object beam and in the reference beam respectively.

9. Spectral interferometry apparatus according to claim 8, wherein the profile of the modulation of the channelled spectrum versus OPD, can be extended in OPD range by increasing the diameters of the two relatively displaced beams.

10. Spectral interferometry apparatus according to claim 8, wherein the said adjustment of extension of the profile of the modulation of the channelled spectrum versus OPD, is accompanied by the adjustment of the lateral displacement, G, of the two relatively displaced beams caused by the displacement optics.

11. Spectral interferometry apparatus according to claim 1, wherein the said object optics is equipped with focusing means to adjust the depth in the target object, $d_f$ where maximum signal is collected from.

12. Spectral interferometry apparatus according to claim 1, wherein in use the combination of the displacement optics and the optical spectrum dispersing optics is arranged such that the profile of modulation of the channelled spectrum versus OPD is narrowed by the focus profile and different depths ranges of the object can be selected by appropriately adjusting the focus.

* * * * *